(12) United States Patent
Sboros et al.

(10) Patent No.: US 11,737,733 B2
(45) Date of Patent: Aug. 29, 2023

(54) METHOD OF, AND APPARATUS FOR, DETERMINATION OF POSITION IN ULTRASOUND IMAGING

(71) Applicant: Heriot-Watt University, Edinburgh (GB)

(72) Inventors: Vassilis Sboros, Edinburgh (GB); Paul Allan Dalgarno, Fife (GB); Konstantinos Diamantis, Edinburgh (GB); Alan Greenaway, Yorkshire (GB)

(73) Assignee: HERIOT-WATT UNIVERSITY, Edinburgh (GB)

(*) Notice: Subject to any disclaimer, the term of this patent is extended or adjusted under 35 U.S.C. 154(b) by 928 days.

(21) Appl. No.: 15/747,060

(22) PCT Filed: Jul. 22, 2016

(86) PCT No.: PCT/GB2016/052232
§ 371 (c)(1),
(2) Date: Jan. 23, 2018

(87) PCT Pub. No.: WO2017/013443
PCT Pub. Date: Jan. 26, 2017

(65) Prior Publication Data
US 2018/0368810 A1    Dec. 27, 2018

(30) Foreign Application Priority Data
Jul. 23, 2015   (GB) .................................. 1513024

(51) Int. Cl.
*A61B 8/08*    (2006.01)
*A61B 8/00*    (2006.01)
(Continued)

(52) U.S. Cl.
CPC ............ *A61B 8/481* (2013.01); *A61B 8/5207* (2013.01); *A61B 8/54* (2013.01); *A61B 8/58* (2013.01);
(Continued)

(58) Field of Classification Search
CPC ......... A61B 8/481; A61B 8/58; A61B 8/5207; A61B 8/54; A61B 8/587; A61B 8/0891;
(Continued)

(56) References Cited

U.S. PATENT DOCUMENTS

2006/0030779 A1    2/2006  Chomas et al.
2006/0052697 A1    3/2006  Hossack et al.
(Continued)

FOREIGN PATENT DOCUMENTS

WO    2015013196 A2    1/2015

OTHER PUBLICATIONS

Written Opinion received in PCT/GB2016/052232 dated Oct. 17, 2016.
(Continued)

*Primary Examiner* — Bo Joseph Peng
(74) *Attorney, Agent, or Firm* — SNELL & WILMER L.L.P.

(57) ABSTRACT

A method of determining a position of a target using a metric comprises receiving a plurality of ultrasound signals representative of ultrasound energy received from the target and, for each of a plurality of different foci, adjusting the ultrasound signals in dependence on the focus and determining a value of the metric using the adjusted ultrasound signals. The method further comprises using the determined values for the metric for the different foci to determine a position of the target.

20 Claims, 11 Drawing Sheets

(51) Int. Cl.
  *G01S 7/52* (2006.01)
  *G01S 15/89* (2006.01)
  *G06T 7/77* (2017.01)
  *G06T 7/571* (2017.01)

(52) U.S. Cl.
  CPC ............ *A61B 8/587* (2013.01); *G01S 7/5205* (2013.01); *G01S 7/52036* (2013.01); *G01S 15/8915* (2013.01); *G06T 7/571* (2017.01); *G06T 7/77* (2017.01); *A61B 8/0891* (2013.01); *G06T 2207/10132* (2013.01)

(58) Field of Classification Search
  CPC . G06T 7/571; G06T 7/77; G06T 2207/10132; G01S 7/52036; G01S 7/5205; G01S 15/8915
  See application file for complete search history.

(56) References Cited

U.S. PATENT DOCUMENTS

| | | | |
|---|---|---|---|
| 2007/0083110 A1* | 4/2007 | Lin | A61B 8/14 600/437 |
| 2008/0228076 A1* | 9/2008 | Azuma | G01S 15/102 600/445 |
| 2009/0306512 A1 | 12/2009 | Loftman et al. | |
| 2010/0324864 A1* | 12/2010 | Vossiek | G01S 13/904 702/151 |
| 2011/0172538 A1 | 7/2011 | Sumi | |
| 2013/0267849 A1* | 10/2013 | Katsuyama | A61B 8/5207 600/443 |
| 2013/0279294 A1* | 10/2013 | Angelsen | A61B 8/485 367/87 |
| 2014/0243667 A1 | 8/2014 | Wilkening | |
| 2016/0018364 A1* | 1/2016 | Rosenzweig | G01N 29/07 73/597 |

OTHER PUBLICATIONS

International Search Report received in PCT/GB2016/052232 dated Oct. 17, 2016.
M. A. O'Reilly, R. M. Jones, and K. Hynynen, "Three-dimensional transcraniai ultrasound imaging of microbubble clouds using a sparse hemispherical array," IEEE Trans. Blom. Eng., vol. 61, No. 4, pp. 1285-1294, 2014.
2) M. A. O'Reilly, and K. Hynynen, "A super-resolution ultrasound method for brain vascular mapping," Med. Phys., vol. 40, No. 11, pp. 110701, 2013.
K. Christensen-Jeffries, R. J. Browning, M. X. Tang, C. Dunsby, and R. J. Eckersley, "In Vivo Acoustic Super-Resolution and Super-Resolved Velocity Mapping Using Microbubbies," IEEE Trans. Med. Imag., vol. 34, No. 2, pp. 433-440, Feb. 2015.
Y. Desailiy, O. Couture, M. Fink, M. Tanter, "Sono-activated ultrasound localization microscopy," Appl. Phys. Lett., vol. 103, No. 17, pp. 174107, 2013.
Dalgarno PA, et al. OSA, Optics Express 2010: 18: 877-884.
Dalgarno HIC et al. J. R. Soc. Interface 2011; 8: 942-951.
Diamantis, K., Voxen, I. H., Greenaway, A. H., Anderson, T., Jensen, J. A. & Sboros, V; A comparison between temporal and subband minimum variance adaptive beamforming; Jan. 1, 2014 Medical Imaging 2014: Ultrasonic Imaging and Tomography. SPIE, vol. 9040, 90400L.
OM Viessmann et al., Acoustic super-resolution with ultrasound and microbubbles.

* cited by examiner

METHOD OF, AND APPARATUS FOR, DETERMINATION OF POSITION IN ULTRASOUND IMAGING

CROSS REFERENCE TO RELATED APPLICATION

This application is a national stage application of PCT/GB2016/052232 filed on Jul. 22, 2016, entitled "A METHOD OF, AND APPARATUS FOR, DETERMINATION OF POSITION IN ULTRASOUND IMAGING", which claims priority to United Kingdom Application No. 1513024.8 filed Jul. 23, 2015, all of which are incorporated herein by reference in their entirety for all purposes.

FIELD

The present invention relates to a method and apparatus for increasing the spatial resolution of ultrasound imaging, for example a method and apparatus for determining a position of microbubbles in ultrasound with a spatial resolution beyond the diffraction limit.

BACKGROUND

The spatial resolution of current ultrasound imaging systems may be determined by the diffraction limit. The interference of emitted wavefronts may reduce the focussing capability of an aperture. Objects that are smaller than the diffraction limit may be resolved, but due to the diffraction of the beam and the duration of transmitted pulses they may appear to have a size of the Point Spread Function (PSF). The PSF may be comparable to the wavelength of the applied sound wave.

The diffraction limit of an ultrasound system may depend on the wavelength of the applied sound wave used, the aperture size, and the duration of transmitted ultrasound pulses. Higher resolution of ultrasound imaging may be achieved by the use of shorter pulses or higher frequencies or by the use of smaller transducer elements, so as to lower the diffraction limit. However, the use of higher frequencies may be at the expense of beam penetration depth. Since attenuation increases with frequency, frequency is inversely related to penetration depth.

High penetration depth, for example a penetration depth in the order of tens of millimetres, may be desired to acquire images of most tissue structures. A trade-off between spatial resolution and penetration depth may be deployed to achieve images of tissue structures that provide diagnostic information. In the axial dimension (which may be considered to be a direction along an axis into the body, for example an axis perpendicular to a transducer array), organs can be imaged using a transmission frequency of a few MHz which may achieve visualisation of several centimetres in depth but may limit the resolution to around the millimetre range. The implementation of frequencies of several hundreds of MHz, which may provide a micrometric resolution, may only allow a penetration depth of less than 1 mm.

Current diffraction-limited diagnostic ultrasound methods are widely used for many diagnostic applications. However, there are cases in which medical ultrasound could provide additional benefits if increased resolution could be achieved. Increased spatial resolution may provide benefits in both diagnostic and therapeutic applications. One example of such an application may be in the detection and characterisation of microvascular diseases. Research towards obtaining high resolution images, for example images of microvascular structure, is being conducted.

Contrast microbubbles may be used in ultrasound imaging. Contrast microbubbles may be micrometre-scale bubbles (for example, bubbles having 2 to 3 µm diameter) that are introduced into vascular structures to be imaged. The reflection of ultrasound waves from microbubbles may be much greater than the reflection of ultrasound waves from soft tissue. Contrast microbubbles may be used to distinguish a vascular structure from the surrounding soft tissue. Microbubbles may be considered to be point targets.

Despite the micrometric size of microbubbles, it may be possible to distinguish single scattering events due to their high scattering efficiency. Microbubble signals may be visualised as microbubbles flow through the vascular bed. Signals may be significantly enhanced by signal processing algorithms that allow the subtraction of all other tissue reflections and scatter. However, the use of high concentrations of microbubbles clinically may provide images where the varying brightness levels can only be measured to provide a qualitative assessment of vascular kinetics.

Some high resolution images of vascular structure have been obtained using contrast agents such as microbubbles, and an a priori knowledge of point source scatter. See, for example, M. A. O'Reilly, R. M. Jones, and K. Hynynen, "Three-dimensional transcranial ultrasound imaging of microbubble clouds using a sparse hemispherical array," IEEE Trans. Blom. Eng., vol. 61, no. 4, pp. 12851294, 2014; M. A. O'Reilly, and K. Hynynen, "A super-resolution ultrasound method for brain vascular mapping," Med. Phys., vol. 40, no. 11, pp. 110701, 2013; K. Christensen-Jeffries, R. J. Browning, M. X. Tang, C. Dunsby, and R. J. Eckersley, "In Vivo Acoustic Super-Resolution and Super-Resolved Velocity Mapping Using Microbubbles," IEEE Trans. Med. Imag., vol. 34, no. 2, pp. 433-440, February 2015. The high resolution images of these studies were accomplished by applying effective aberration correction methods based on high accuracy position estimation of individual bubbles.

With the exception of the studies cited above, the use of super-resolution imaging may still be considered to be limited in medical ultrasound when compared to other imaging fields that are also diffraction limited, such as optical microscopy. Resolution of ultrasound images may in most cases be comparable to the wavelength used.

SUMMARY

In a first aspect of the invention, there is provided a method of determining a position of a target using a metric, the method comprising receiving a plurality of ultrasound signals representative of ultrasound energy received from the target; for each of a plurality of different foci, adjusting the ultrasound signals in dependence on the focus and determining a value of the metric using the adjusted ultrasound signals; and using the determined values for the metric for the different foci to determine a position of the target.

The determined position of the target may be a depth position of the target.

A spatial resolution of the determining of the position of the target may be below a diffraction limit for a frequency of the ultrasound signals.

In ultrasound, it may be possible to obtain multiple sets of processed data, each processed using a different focus, from signals obtained from a single transmission. By processing a set of ultrasound signals using multiple foci, a high position resolution may be obtained, for example a resolution beyond the diffraction limit.

The plurality of ultrasound signals may represent ultrasound energy received from a single ultrasound transmission. Several different values for the metric may be obtained from data from a single ultrasound transmission. The different values for the metric may be obtained by adjusting the signals differently for each focus.

The metric may be based on at least one of a sharpness, a contrast, an intensity, a signal amplitude.

The determined value for the metric may be different when the ultrasound signals are processed using different foci. The difference in values of the metric for the different foci may be used in determining position.

For each focus, adjusting the ultrasound signals may comprise focusing the ultrasound signals at the focus. Each focus may comprise a focal point or focal plane.

Adjusting the ultrasound signals in dependence on the focus may comprise beamforming the ultrasound signals, for example at the focus. Adjusting the ultrasound signals in dependence on the focus may comprise beamforming the ultrasound signals in receive, using the focus as a receive focus.

Beamforming the ultrasound signals, for example at the focus, may comprise applying time delays to at least some of the ultrasound signals.

The plurality of ultrasound signals may correspond to a respective plurality of ultrasound transducer elements, and the time delays may be applied in dependence on a distance from each transducer element to the focus.

The beamforming of the ultrasound signals at the focus may comprise using a Delay-and-Sum beamformer. Beamforming the ultrasound signals may comprise summing the time-delayed ultrasound signals. Different time delays may be applied to focus the signals at different foci.

Beamforming the ultrasound signals may further comprise applying apodization weights to the ultrasound signals.

Using the determined values for the metric for the different foci to determine a position of the target may comprise using a plurality of calibration functions, each calibration function corresponding to a respective focus.

For each focus, the corresponding calibration function may be a function of position of the target and value for the metric with that focus.

For each focus, value for the metric may vary with position. For a given position, the value for the metric for one focus may be different for the value for the metric for another focus. Therefore a plot of value of the metric versus position may be different for each focus.

Each calibration function may be obtained from measurements and/or simulations of the value of the metric for a target that is placed at a plurality of positions.

The determined position for the target may be a position for which the determined values of the metric for the different foci best match calibration function values of the metric for that position.

Each calibration function may comprise a probability density function.

The probability density function may be a function of mean values for the metric and variances or standard deviations for values of the metric. The probability density function may comprise a likelihood or probability for value of the metric with target position.

Determining the position of the target may comprise determining a position for which a combination of the calibration functions is maximised.

The combination of the calibration functions may comprise a product of the calibration functions. Each calibration function may comprise a likelihood or probability that a target in a given position will result in a given value of the metric. The likelihoods or probabilities may be independent of each other.

Determining a position for which a combination of the calibration functions is maximised may comprise using a maximum likelihood estimator.

The metric may comprise a sharpness metric. A sharpness metric may be representative of the total aberration that is dominated by defocus, in a data set. A value for a sharpness metric may be higher for a target that is in focus than for a target that is out of focus.

The adjusted ultrasound signals may comprise a plurality of data points. The value for sharpness metric may be dependent on amplitudes for a selected at least some of the plurality of data points.

Each data point may correspond to a different position in coordinate space. Adjusting the ultrasound signals may comprise beamforming the ultrasound signals for each focus. The beamformed signals may be represented by the plurality of data points. The data points may be referred to as samples. The selected at least some of the plurality of data points may be data points in a region around the target.

The method may further comprise performing an envelope detection on the adjusted ultrasound signals (for example, the beamformed ultrasound signals). The envelope detection may comprise a Hilbert transform. The amplitudes for the data points may comprise envelope values for the data points.

The sharpness metric may be proportional to the fourth power of the amplitudes of the selected at least some of the plurality of data points.

The sharpness metric may be a normalised sharpness metric. Determining the sharpness metric may comprise summing the fourth power of the amplitudes of the selected data points, and dividing by a square of the sum of the squares of the amplitudes of the selected data points.

The method may further comprise selecting a region around the target, wherein the metric is determined for the selected region.

Determining the metric for only a selected region may be more efficient than using all the data from the ultrasound signals. More than one target may be represented in received data, and a separate region may be determined for each target.

The selected at least some of the plurality of data points may be data points within the selected region.

The method may further comprise determining statistics for the data points within the selected region, and adjusting the selected region based on the determined statistics. The statistics may comprise, for example, a range or distribution of amplitude values. Adjusting the selected region may comprise changing a size, shape and/or position of the selected region. For example, the statistics may indicate that the selected region contains more than one target, in which case the size of the selected region may be reduced.

The same selected region may be used in determining the value of the metric for each focal point.

Selecting a region around the target may comprise determining an approximate position for the target and selecting a region around the approximate position.

Determining an approximate position may comprise determining a maximum or minimum in at least one property of the adjusted ultrasound signals. The at least one property may comprise amplitude. The approximate position may be determined from the adjusted ultrasound signals. The approximate position may be determined from the adjusted ultrasound signals for a single focus. Determining an approximate position may comprise detecting a peak or PSF (point spread function) and centering the selected region on the peak or PSF.

The target may comprise a contrast microbubble. The contrast microbubble may be considered to be a point source. The contrast microbubble may comprise a gas-filled microbubble. The contrast microbubble may comprise, for example, a sulphur hexafluoride bubble with a phospholipidic monolayer shell. The contrast microbubble may comprise a Sonovue® microbubble.

The ultrasound signals may be received from an ultrasound transmission, the ultrasound transmission comprising a non-linear ultrasound pulse. The non-linear pulse may be such that ultrasound signals received from the contrast microbubble are enhanced when compared with ultrasound signals received from soft tissue.

The determined position of the target may comprise an axial position. The different foci may be focal points having different positions in an axial direction. The position of the target in an axial direction may be determined by obtaining values for the metric for focal points having different axial positions.

The target may be part of an object to which ultrasound energy is transmitted from an ultrasound source, and the axial direction may be a direction into the object from the ultrasound source.

The axial position may be a position in depth. The axial position may comprise a distance from the ultrasound source, for example a distance from a central element of a linear array transducer.

The ultrasound source may comprise an ultrasound transducer. The ultrasound signals may be received by the ultrasound transducer. The determined position may be a position in an axial direction with respect to the ultrasound transducer. The ultrasound transducer may be a linear array extending in a lateral direction.

The ultrasound signals and/or the adjusted ultrasound signals may comprise raw ultrasound data.

For each focus, the value of the metric may be determined from raw ultrasound data. The value of the metric may be determined without forming an image from the ultrasound data. Raw ultrasound data may comprise data that has not been compressed and/or interpolated. The determination of the metric may be more accurate when performed on the raw ultrasound data than when performed on data that has been processed to form an image, for example by compression and/or interpolation.

The method may further comprise processing the ultrasound signals to form an image of the target using the determined position of the target.

The method may further comprise determining the position of at least one further target using the metric. Determining the position of the at least one further target may comprise determining values of the metric for the further target. A region around the further target may be selected, and the values of the metric may be determined for that region.

In a further aspect of the invention, which may be provided independently, there is provided an apparatus for determining a position of a target using a metric, the apparatus comprising a receiver, for example an ultrasound transducer, configured to receive a plurality of ultrasound signals representative of ultrasound energy received from the target; and a processor, wherein the processor is configured to, for each of a plurality of different foci, adjust the ultrasound signals in dependence on the focus and determine a value of the metric using the adjusted ultrasound signals; and wherein the processor is further configured to use the determined values for the metric for the different foci to determine a position of the target.

In a further aspect of the invention, there is provided a method of calibration of a position determination method using a metric, the method comprising: for each of a plurality of foci, determining a calibration function of value of the metric and position for that focus by positioning a target at each of a plurality of known positions and, for each of the plurality of known positions, determining a value of the metric for the target at the position by: receiving a plurality of ultrasound signals representative of ultrasound energy reflected from the target, adjusting the ultrasound signals to focus the signals at the focus, and determining a value of the metric for the target using the adjusted ultrasound signals.

By positioning a target at a plurality of known positions and determining values of the metric for those positions, a calibration function may be obtained. The ultrasound signals may be received from an ultrasound transmission. For each position, a plurality of values for the metric for a given focus may be obtained by using multiple ultrasound transmissions and obtaining a value of the metric from each transmission. Statistical data for the value of the metric may be obtained. The calibration function may be determined using statistical data, for example mean and variance for the value of the metric.

There may be provided a method or system substantially as described herein with reference to the accompanying drawings.

Features in one aspect may be provided as features in any other aspect as appropriate. For example, features of a method may be provided as features of an apparatus and vice versa. Any feature or features in one aspect may be provided in combination with any suitable feature or features in any other aspect.

DETAILED DESCRIPTION OF EMBODIMENTS

Embodiments of the invention are now described, by way of non-limiting example, and are illustrated in the following figures, in which:—

Figure 1:
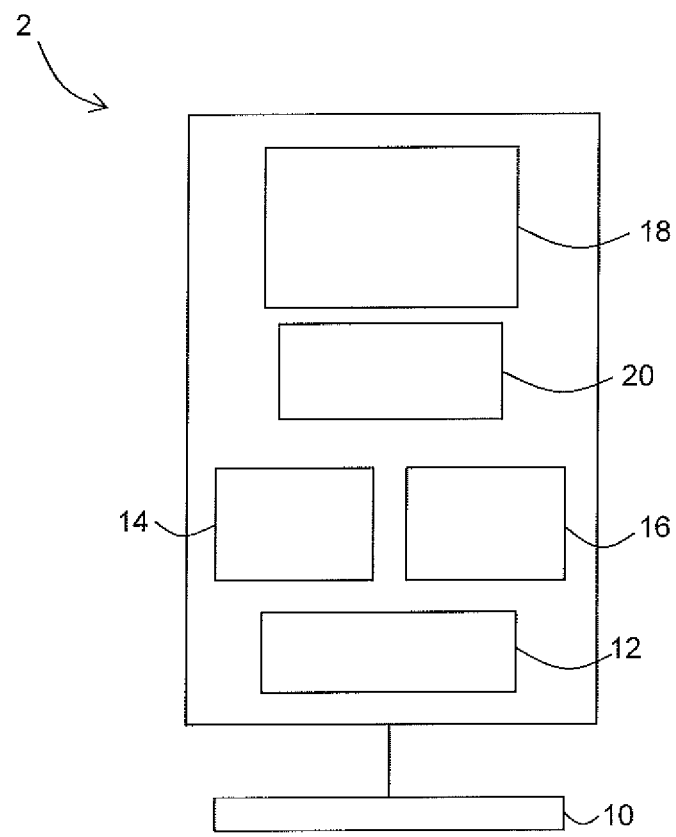
FIG. 1 is a schematic diagram of an ultrasound imaging apparatus.

An embodiment of an ultrasound imaging apparatus 2 is illustrated schematically in FIG. 1. A linear array transducer 10 is configured to transmit energy into an object to be imaged (for example, a part of the human or animal body) and to receive ultrasound echoes from the object. In other embodiments, any suitable transducer may be used to receive 2D or 3D ultrasound data.

The received ultrasound echoes are digitized by an analogue to digital converter (ADC) 12. The digitized ultrasound data is stored in memory 16.

The digitized ultrasound data is processed by a processor 14 and the resulting processed data may also be stored in memory 16, or in another memory. The processor 14 may be configured to perform beamforming of the digitized echo data. In some embodiments, more than one processor 14 may be used.

The ultrasound imaging apparatus 2 also includes a screen 18 for the display of ultrasound images and one or more user input devices 20 (for example, a keyboard, mouse or trackball) for receiving input from a user of the ultrasound imaging apparatus 2, for example a sonographer.

In the embodiment of FIG. 1 the ultrasound imaging apparatus 2 is configured to obtain ultrasound data using the linear array transducer 10 and to process that data. In other embodiments, a separate processing apparatus (for example, a workstation or general purpose computer) may be used to process ultrasound data that has previously been acquired by an ultrasound machine.

The ultrasound imaging apparatus 2 is configured to perform super-resolution imaging of targets that may be considered as point sources. The targets may be, for example, contrast microbubbles.

The ultrasound imaging apparatus 2 is configured to determine the position of a target by determining multiple sharpness values for the target from a single ultrasound data set, obtained from a single ultrasound transmission. The different sharpness values are determined by beamforming the ultrasound data using different focal points. The most likely position of the target may be determined by comparing the different sharpness values to curves of sharpness versus position. In other embodiments, a metric other than sharpness is used.

A method of determining position of a target from multiple sharpness values obtained from a single ultrasound transmission is now described with reference to a simulation. A calibration method (described below with reference to FIG. 3) is performed by placing a simulated target at each of a plurality of positions in the axial (z) dimension and calculating multiple sharpness values from the simulated data for each position. The simulation is repeated several times with noise added to the simulation so that statistical data may be obtained. The sharpness values are used to create sharpness curves and probability density functions for sharpness value versus position.

A position determination method (described below with reference to FIG. 7) is then performed in which positions of the target are estimated by maximum likelihood estimation using the determined probability density functions from the calibration method. The estimated positions are compared to the actual positions for which the simulation was performed, to determine an accuracy for the determination of position.

Figure 2:
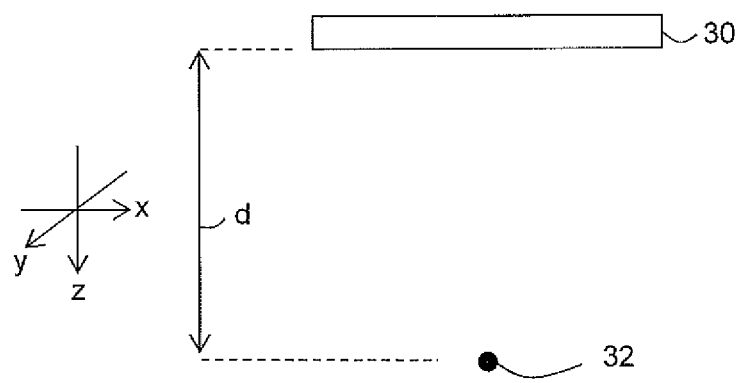
FIG. 2 is a schematic diagram of a simulated transducer and simulated point source.

FIG. 2 is a schematic diagram showing the simulated transducer 30 and point source 32. Although in the diagram of FIG. 2 the point source 32 is represented by a filled circle in the x and z plane, in the simulation the point source 32 is a single point. FIG. 2 also shows x, y and z axes, and a distance d between the simulated transducer 30 and simulated target 32.

Figure 3:
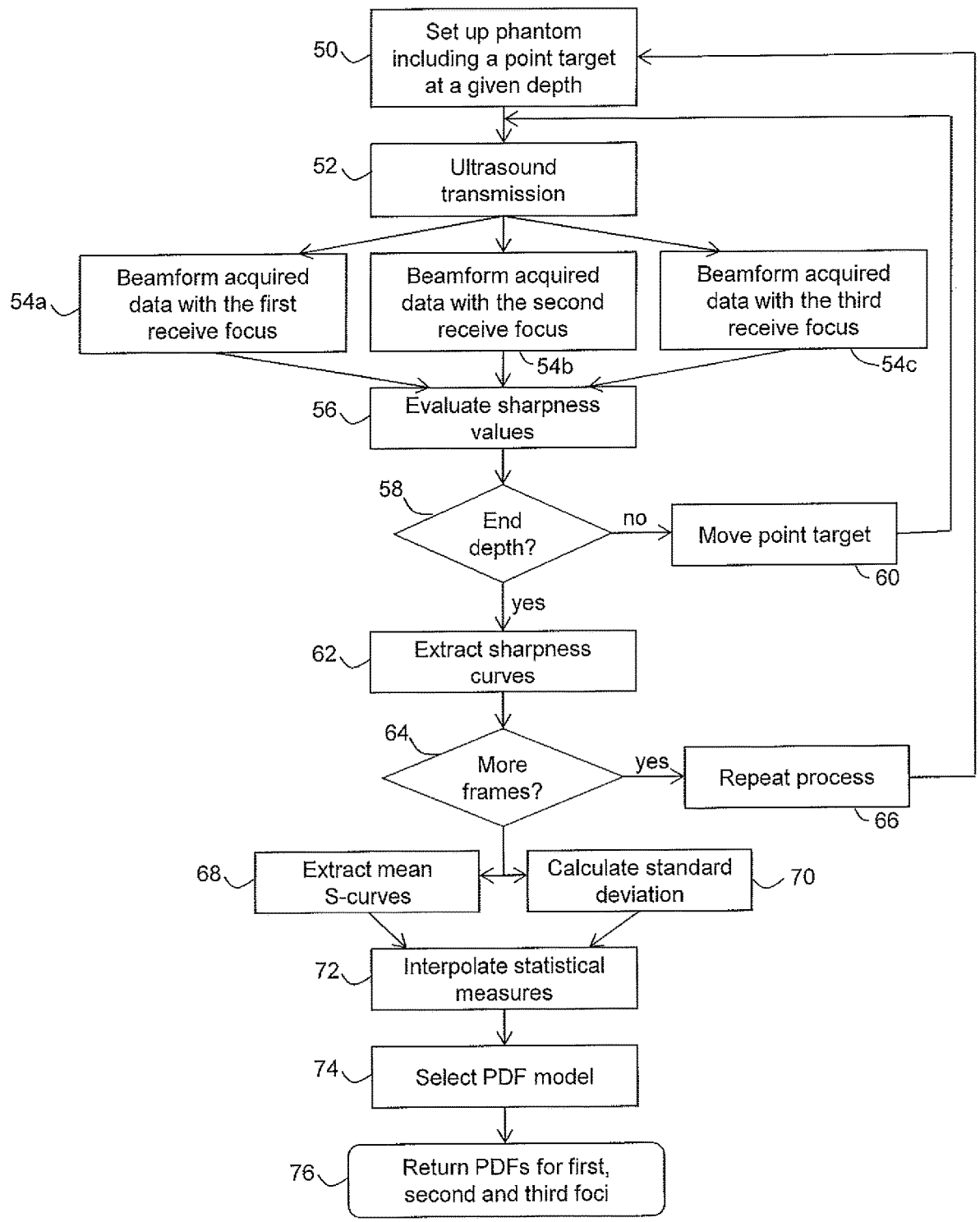
FIG. 3 is a flow chart of a calibration process according to an embodiment.

FIG. 3 is a flow chart that is representative of a calibration method. Although FIG. 3 is initially described with reference to simulated data, the process of FIG. 3 may also be used for calibration of a method that may be used for real data, for example for experimental data or medical imaging data.

At stage 50 of the flow chart of FIG. 3, a simulated target 32 is positioned at an initial position in relation to a simulated transducer 30. In the present simulation, the simulated target is a single point scatterer. The simulated target may also be referred to as a phantom. Only one simulated target 32 is used in this simulation. In other simulations, or in embodiments using real data, multiple targets may be present. Each target may be represented as a point source.

It will be understood that the simulation is performed as a computation using simulation software and that, for example, references to positioning and to signals in the following discussion refer to virtually positioning items in a simulation, and to virtual signals generated by the simulation. In the present example, the simulation is carried out with Field II software, and Matlab scripts have been written for data post-processing. Since the simulation software, Field II, would produce identical results from repetitive simulations, 10 dB white Gaussian noise is added to the raw data to introduce a level of uncertainty.

In the present simulation, the transducer that is simulated is a 7 MHz, 192 element, linear array transducer. The spacing between the elements of the simulated transducer is 208 μm, which is close to the ultrasound wavelength, λ. In this simulation, the wavelength λ is 220 μm. The speed of sound is set to 1540 m/s. Parameters of the simulated ultrasound scan are given in Table 1.

| Transducer | |
|---|---|
| Transducer type | Linear array |
| Transducer element pitch | 208 μm |
| Transducer element kerf | 35 μm |
| Transducer element height | 4.5 mm |
| Centre frequency, $f_0$ | 7 MHz |
| Bandwidth | 60% fractional |
| Speed of sound, c | 1540 m/s |
| Wavelength, $\lambda = c/f_0$ | 220 μm |
| Excitation pulse | Two-cycle sinusoid at $f_0$ |
| Plane wave emission | |
| Transmit apodization | Hanning |
| Receive apodization | Hanning |
| Receive focus depth | 39 mm/40 mm/41 mm |
| Number of transmitting elements | 192 |
| Number of receiving elements, M | 192 |
| Number of emissions | 1 |
| Particle movement | |
| Highest point | (x, z) = (0, 32.5) mm |
| Lowest point | (x, z) = (0, 47.5) mm |
| Total distance covered | 15 mm (axially only) |
| z step between successive emissions | 0.1 mm |

In the present simulation, the initial position of the simulated target 32 is z=40 mm (distance d In FIG. 2 is 40 mm). The x and y coordinates of the simulated target 32 are (x=0, y=0). The x and y coordinates of the simulated target 32 remain at (x=0,y=0) throughout the process of FIG. 3.

At stage 52, an ultrasound transmission is simulated, in which a single unfocussed plane wave emission is transmitted by the transducer 30 towards the target 32. In this case, a single plane wave means that all transducer elements are active in transmit. Each transducer element is transmitting an unfocused sound wave.

The use of a single plane wave is in contrast to a common ultrasound transmission which may involve a group of active elements (a subset of the transducer elements) that transmit a focused beam. In the common ultrasound transmission, after a reception, the active aperture is moved across the array and a new focussed beam is transmitted. A final image results from combining all received responses. In contrast, responses from a single plane wave transmission may be used to form an entire image.

Using a plane wave transmission may be faster than using successive emissions from different groups of elements. An unfocussed beam may cover the whole image region with only one emission, which may allow for a high frame rate and multiple acquisitions.

Reflected ultrasound signals are received by each element of the transducer 30. Raw data from the single unfocussed emission is acquired for all 192 channels (192 transducer elements) individually in receive. Data acquisition is performed at a given sampling frequency. In the present simulation, the ultrasound signal received by each transducer element is a signal comprising 2000 samples.

The sampling frequency for the simulations is 100 MHz. In some circumstances, it may not be possible to reach a sampling frequency of 100 MHz in an experiment but the sharpness calculation described may not be substantially affected by a lower sampling frequency. In the experiment described below, the sampling frequency is 70 MHz.

Receive processing is then utilized to achieve multi-focal data (for example, data that may be used to create multi-focal images). The transducer element signals can be beamformed offline in multiple ways. One such method is described below, in which received signals are processed using a Delay-and-Sum beamformer. The signals are time-delayed, weighted and summed to form a maximized beamformer output.

At stages 54a, 54b and 54c, the ultrasound data for the target 32 positioned at 40 mm is beamformed using three different focal points in receive. At stage 54a, the ultrasound data is beamformed with the first focal point. The first focal point is x=y=0, z=39 mm. At stage 54b, the ultrasound data is beamformed with the second focal point. The second focal point is x=y=0, z=40 mm. At stage 54c, the ultrasound data is beamformed with the third focal point. The third focal point is x=y=0, z=41 mm.

The transducer element signals are beamformed using a Delay-And-Sum beamformer. The input to the Delay-and-Sum beamformer is a matrix of 192×2000 samples (signals received by 192 elements, with each received signal comprising 2000 samples).

In the Delay-and-Sum beamformer, the signals are time-delayed to account for the fact that different elements are different distances from the focal point.

For M receive elements numbered from m=0 to m=M-1, a time delay of $\tau_m$ is the time delay applied to the mth receiving element. The time delay applied to each receiving element depends on the distance of the receiving element from the focal point.

Each time delay may be calculated using the equation below:

$$\tau_m \propto \frac{r_p \sin \theta_m}{c} \quad \text{(Equation 1)}$$

$r_p$ is the position of the focal point. c is the speed of sound. $\theta_m$ is an angle formed by the mth element, the central element, and the focal point.

In the present simulation, apodization weights are also used to alter the shape of the beam and account for the array being finite. Apodization weights may have the effect of reducing sidelobes. In the present simulation, Hanning weights are used. Any appropriate apodization weights may be used.

The beamformer output, B(t) for an array probe with M active elements in receive may be extracted by:

$$B(t) = \Sigma_{m=0}^{M-1} w_M(t) x_m(t-\tau_m) = w(t)^H X(t) \quad \text{(Equation 2)}$$

where t is the time index, $w(t)=[w_0(t), w_1(t), \ldots, w_{M-1}(t)]^H$ is the vector of the apodization weights, $X(t)=[x_0(t-\tau_0), x_1(t-\tau_1), \ldots, x_{M-1}(t-\tau_{M-1})]^H$ is the array of the transducer element signals, and $\tau_m$ is the time delay applied to the mth receiving element, based on its distance from the focal point.

It can be seen from Equation 1 and Equation 2 that B(t) can be calculated for any focal point $r_p$. Equations 1 and 2 can be implemented separately for any $\tau_m$, thus foci in receive. Three (or any number of) different receive foci can be implemented. Three different receive foci will result in three different beamformer outputs that are capable of subsequently being processed to produce different images of the same object.

The output of the beamformer is a set of samples, each corresponding to a specific (x, z) position. The matrix of samples returned by the beamformer has the same dimensions as the matrix of samples that is input to the beamforming equation, i.e. 192 points in x by 2000 points in z.

The total x range for which the beamformed data is calculated is the same as the lateral extent of the linear array transducer. In this simulation, the lateral extent of the transducer is 4 cm. Samples are determined for x values corresponding to the x positions of the elements of the transducer, i.e. for 192 equal steps in x ranging from −2 cm to +2 cm.

The number of samples in the z direction depends on the sampling frequency with which the ultrasound data is acquired (since position in the z direction corresponds to time). In the present simulation, there are many more samples axially than laterally.

A Hilbert transform, which is an envelope detection, is performed for each sample to obtain an amplitude for that (x, z) position. The amplitude of the sample is the envelope value of the sample.

The time delays applied in Equation 2 are different for the three focal points of stages 54a, 54b and 54c since the time delays are dependent on the distances of the elements from the focal point. The apodization weights are the same for stages 54a, 54b and 54c.

Stages 54a, 54b and 54c may be performed simultaneously or sequentially. Stages 54a, 54b and 54c are all performed on the same data (the data received from the simulated transmission of stage 52). The output of stages 54a, 54b and 54c is first, second and third sets of beamformed data. Each set of beamformed data has undergone a Hilbert transform. Each set of beamformed data comprises a set of samples for a plurality of (x, z) positions, each sample having an associated amplitude value which is the envelope value at that sample.

It is possible to create an image from the beamformed data on which the Hilbert transform has been performed. However, in the present method, the data used in subsequent steps of the process of FIG. 3 is data as obtained after the Hilbert transform, which may be described as raw data, and is not further processed to form an image.

If an image is to be generated and/or displayed, the set of beamformed data after the Hilbert transform may undergo logarithmic compression to reduce its dynamic range. The logarithmically compressed data may be displayed as an image, for example as a Matlab figure. In order to save an image, it may be converted into square pixels. Interpolation or conversion of the data may be performed. The data may be converted into any suitable image format.

Turning again to the flow chart of FIG. 3, at stage 56 a sharpness value for each of the three sets of beamformed data (one data set per focal point) is evaluated. The sharpness value used in the simulation is a value for a particular sharpness metric, as described below. In other simulations or embodiments, a different sharpness metric may be used, or a metric that does not measure sharpness, for example a metric related to contrast or intensity.

In general, a sharpness metric may be a single metric that describes the total aberration in a system. A sharpness metric may be maximal where the aberration is minimal. A sharpness metric may be strongly dependent on defocus. A value for the sharpness metric may fall rapidly as defocus is increased. A sharpness metric may reach its maximum value for an in-focus image. A number of different ways to assess the sharpness function are available. The definition of a sharpness metric may be, at least in part, dependent on an application for which the sharpness function is used.

A region around the target 32 is selected. In the present simulation, the region is a square in (x, z) around the target 32. The square has dimensions of 2.3 mm×2.3 mm. A square of this size may correspond to using signals from 5 elements on either side of the point target (11 signals in total). In other examples, any shape of selected region may be used, for example a rectangular, square or circular region of any appropriate size. The size of the selected region may be such as to contain the main lobe of the point target. The selected region may be centred on the point target.

Samples that are within the selected region are used for the evaluation of sharpness. The same region is selected for each of the three sets of beamformed data (one set of beamformed data for each focus point). The data samples used for the evaluation of the sharpness are raw data, i.e. data that has been obtained after beamforming and the Hilbert transform, and has not been compressed or interpolated. The data samples are samples from the sets of beamformed data as output from stages 54a, 54b and 54c above.

In optics, image sharpness may be obtained from image pixel intensities. Image sharpness may in some circumstances be estimated by summing the squared values of each pixel and then normalized by dividing by the squared sum of all pixel intensities. In optical applications, sharpness may in some circumstances be defined for a region including a point source as the sum of the square over all pixels of the region, biased by the pixel value and normalized by total pixel values over the region. The bias term may account for low photon count in optical data.

In ultrasound imaging, it is possible to access the data from which an ultrasound image may be formed (for example, the sets of beamformed data that are the output of stages 54a, 54b and 54c). In this simulation, sample amplitudes are used for calculation of sharpness instead of pixel intensities.

Image intensity may be generally proportional to the square of signal amplitudes. The sharpness metric used in optics may be proportional to the square of pixel values.

In the present calculation, amplitudes of the received transducer elements are used (instead of image intensity). The sharpness metric may be proportional to the fourth power of signal amplitudes.

In the present embodiment, the sharpness metric used is:

$$S = \sum_{k=1}^{q} E_k^4 / (\sum_{k=1}^{q} E_k^2)^2 \quad \text{(Equation 3)}$$

S is the normalized sharpness calculated from the RF data. The samples in the selected region are numbered as k=1 to q. $E_k^2$ is the squared envelope value of the kth sample.

In other embodiments, the sharpness calculation may be performed before the envelope detection. However, sharpness curves may be smoother if the sharpness values are calculated after envelope detection.

The sharpness value for each of the three sets of beamformed data (each having a different focal point) is determined using Equation 3 for the samples in the selected region. Three sharpness values are obtained at stage 56, with each sharpness value being associated with a respective focal point.

At stage 58, the simulation determines whether there are axial positions of the target for which measurements have not yet been made. Since the only axial position for which measurements have been made is the initial position of z=40 mm, a new iteration of the simulation is created in which the position of the target 32 is moved by a z increment in the direction away from the transducer 30. The z increment is 0.1 mm.

At a second iteration of stage 52, a further ultrasound transmission is simulated with the target now positioned at z=40.1 mm. At the second iteration of stages 54a, 54b and 54c the data from the further ultrasound transmission is beamformed using first, second and third receive foci at z=39 mm, 40 mm and 41 mm and an envelope detection is performed to obtain first, second and third sets of beamformed data. At the second iteration of stage 56, values of sharpness are evaluated for each of the receive foci using Equation 3.

The region on which the sharpness is calculated in the second iteration of stage 56 may be different from the region which was selected for the sharpness calculation at the initial position in the first iteration of stage 56. The region on which the sharpness is calculated may be shifted in z such that the selected region is centred on the new z position of the target 32.

At this point in the process of FIG. 3, three values of sharpness are known for a target position of z=40 mm, and three values of sharpness are known for a target position of z=40.1 mm.

The process moves to a second iteration of stage 58. The simulation determines that there are more depths (z positions) for which sharpness is yet to be calculated. The process passes to stage 60 again and a new simulation is created with the target 32 positioned at z=40.2 mm. Stages 52 to 56 are repeated for the new z position.

Stages 52 to 60 are repeated with increasing values of z until a position of 47.5 mm is reached. Stages 52 to 60 are then repeated with decreasing values of z from 39.9 mm to 32.5 mm.

In all, stages 52 to 58 are repeated for 151 steps, i.e. 151 different z positions, each separated by a step of 100 µm. A single point scatterer is moved across the axial direction with a controlled step, and raw scatter data for each position is captured. The process is repeated until the scatterer covers a distance of several millimetres.

There are 151 simulated acquisitions overall with the point target 32 covering a distance of exactly 15 mm. For each acquisition the data are beamformed with three different foci in receive. The central receive focus has been selected with a depth of 40 mm, that is, at the target's initial position. The other two values for the receive focus are at −1 mm and +1 mm of the starting depth.

All sharpness values plotted together over the point total displacement may create three sharpness curves. At stage 62, sharpness curves are extracted from the sharpness data that has been acquired for the 151 z positions at which the target 32 was positioned.

A set of three normalized sharpness values is calculated from each of the 151 acquired data sets, leading to the generation of three sharpness curves (which may also be called S-curves).

One S-curve is generated for each focal point, using the normalized sharpness values calculated from each of the 151 acquired data sets. The S-curve for a given focal point relates sharpness value to target position. The S-curve may be represented by a plot of sharpness value versus target position for that focal point. A Lorentzian function is fitted to each of the S-curves.

At stage 64, the simulation determines whether more frames are required. If so, at stage 66 it instructs the process to be repeated, and the process returns to stage 50. Stages 50 to 62 are repeated as described above. Further sets of beamformed data are produced, and further sharpness values are obtained for 3 focal points at each of 151 positions. The further sharpness values are used to produce further S-curves.

In this case, the simulation is repeated such that it is performed 5 times in total. Field II would produce identical results if the simulation were repeated exactly. To introduce a level of uncertainty, 10 dB white noise is added to the raw data. Therefore, each repetition of the simulation may return somewhat different results. By adding noise to the simulation, it is possible to extract mean S-curves and their variance as described below. The mean and variance may then be used in MLE (maximum likelihood estimator) analysis.

At stage 68, for each of the three focal points, the processor 14 extracts a mean S-curve from the repetitive measurements (5 iterations, each providing sharpness values for 151 z positions). For each position, 5 different values of sharpness have been obtained for a given focal point. A mean sharpness value is calculated for the position, which is the mean of the 5 sharpness values. A mean S-curve is calculated for each focal point. The mean S-curve is a curve of mean sharpness value versus target position. A Lorentzian fit is then applied to the mean curves. The Lorentzian function may be a good approximation of the S-curve peak.

Figure 4:
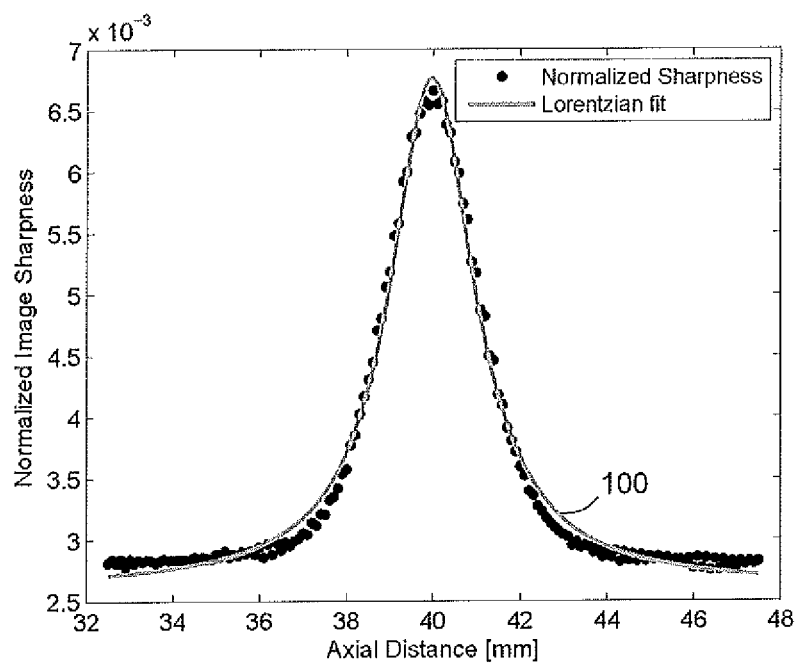
FIG. 4 is a plot of a mean sharpness curve with Lorentzian fit.

FIG. 4 is an example of a single S-curve having a receive focus at 40 mm. The single S-curve is a mean S-curve for a single focal point (40 mm). Normalized sharpness values are plotted against the total displacement (illustrated as d in FIG. 2) of the target. Each mean sharpness value is represented as a point on FIG. 4.

FIG. 4 also shows the Lorentzian fit (line 100) of the mean S-curve that is illustrated in FIG. 4. The correlation coefficient between the mean S-curve and the Lorentzian fit is 0.99.

The value of the sharpness metric changes when a single scatterer moves closer or away from focus. It may be seen from FIG. 4, which has a focal point at 40 mm, that the sharpness value peaks at the focal point and falls off as the target 32 moves further away from the focal point.

At stage 70, for each focal point, the simulation determines a variance of the sharpness values for each position. Stage 70 may occur at the same time or before or after stage 68.

Figure 5:
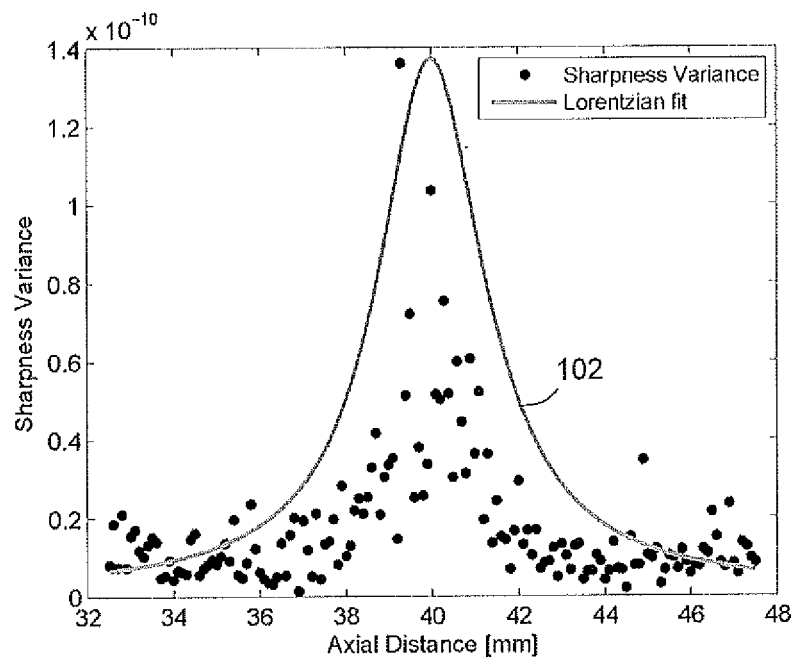
FIG. 5 is a plot of variance with Lorentzian fit.

FIG. 5 is a plot of the sharpness variance of the S-curve of FIG. 4. Variance is plotted over the total displacement d of the target. A Lorentzian function is fitted to the variance. The Lorentzian fit to the variance is shown as line 102. The correlation coefficient between the variance curve and the Lorentzian fit is 0.78.

The sharpness variance demonstrates that, with the addition of noise, Field II data from successive simulations is similar but not identical. It may be seen that higher values of variance are present around the S-curve peak, and lower values of variance are present closer to the edges of the curve.

Figure 6:
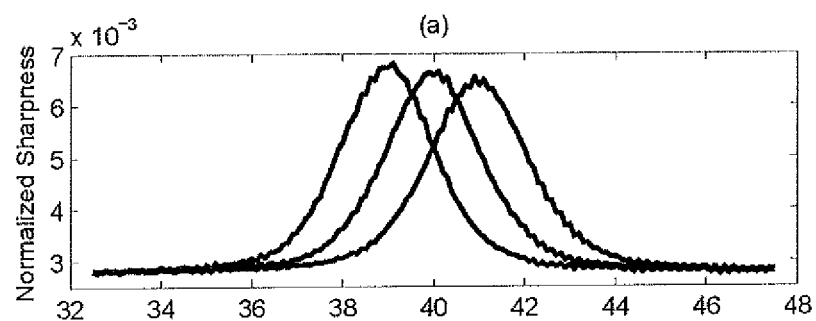
FIG. 6 is a plot of three sharpness curves.

FIG. 6 shows three sharpness curves for Field II data of a point scatterer target 32 moving in depth. Each curve has been generated after beamforming the same data with a different focus in receive.

It may be seen that, at least for depths around the initial position at 40 mm, a target at a given depth is likely to have a different sharpness value when beamformed with each focal point. For example, a target positioned at 39 mm may have a sharpness value of $6.68 \times 10^{-3}$ when beamformed with a focal position of 39 mm, a sharpness value of $5.18 \times 10^{-3}$ when beamformed with a focal position of 40 mm, and a sharpness value of $3.64 \times 10^{-3}$ when beamformed with a focal position of 41 mm.

The mean S-curves generated at stage 68 and the variances calculated at stage 70 are used as inputs to stage 72.

At stage 72 the simulation interpolates the Lorentzian fits of the mean S-curves and variance to a large number of z positions. In the present simulation, the Lorentzian fits of the mean S-curves and variance are interpolated by a factor of 1000. The interpolation is performed using the Matlab spline interpolation function.

At stage 74, for each focal point, the interpolated Lorentzian fits of the mean S-curve and variance for that focal point are used in the estimation of a probability density function (PDF) for that focal point.

Data from all of the repetitive simulations are used in the estimation of the PDFs. Each probability density function, $P(S_j|z)$, is the probability that a specific normalized sharpness value, $S_j$, will be measured from the raw ultrasound data of a point source located at depth z, where j denotes the focus in receive.

A Gamma distribution is selected for the PDF. The Gamma distribution may fit well with the Lorentzian shaped S-curves and their variance. The interpolated Lorentzian fit for the mean sharpness and the interpolated Lorentzian fit for the variance are inserted into the selected Lorentzian-Gamma PDF (see Equation 4 below).

For each focal point, the PDF for that focal point is given by:

$$P(S_j|z) = \frac{e^{\bar{S}_j^2} \bar{s}_j^{\alpha-1} \beta^{-\alpha}}{\Gamma(\alpha)} \qquad \text{(Equation 4)}$$

where $\alpha = \bar{S}_j^2(z)/\bar{\sigma}_j^2$ and $\beta = \bar{\sigma}_j^2/\bar{S}_j^2(z)$.

$\bar{S}_j(z)$ represents the interpolated Lorentzian fit for the mean S-curve for the jth focal point. $\bar{\sigma}_j^2$ represents the interpolated Lorentzian fit for the variance for the jth focal point. $\bar{S}_j(z)$ and $\bar{\sigma}_j^2$ are each extracted from the repetitive simulations. P is the Gamma function.

At stage 76, the process of FIG. 3 returns a set of PDFs. One PDF is returned for each focal point. For example, in the present simulation, three PDFs are returned. Each PDF expresses, for a given focal point, a probability or likelihood that a given sharpness value results from a given z position.

The PDFs may be used to determine a z position of a target from its sharpness values (for example, as described below with reference to FIG. 7). The objective of the position determination method is to provide a unique estimate for each point scatterer position. The estimate may have increased accuracy since each position may be characterized by three distinct sharpness values.

If only a single S-curve were available, there may be an ambiguity in determination of position from that one S-curve, since typically two positions may return the same sharpness value. By using multiple S-curves, position may be uniquely determined for some range of position.

The accuracy of the estimation is determined and an error is extracted. In the simulation, all z positions are known because they are required in order to set up the simulation. However, the method of FIG. 7 is used to determine an estimated position for the target in each acquisition by using the multiple sharpness values obtained by beamforming with different focal positions. The estimated position of the target is then compared to the actual position of the target in the simulation to determine an accuracy for the method of position determination.

Figure 7:
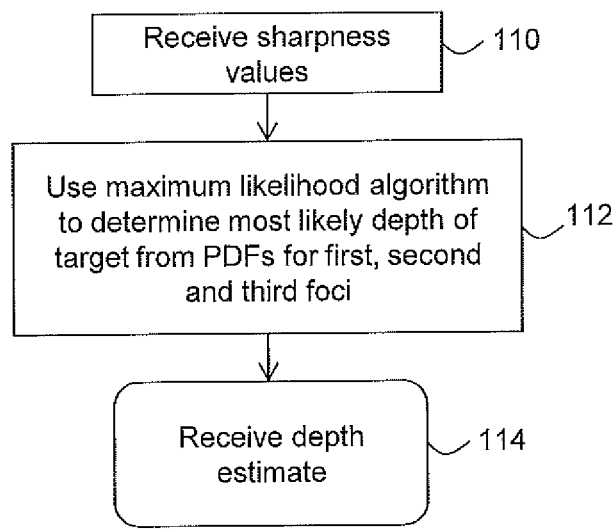
FIG. 7 is a flow chart of a process according to an embodiment.

A set of three sharpness values as measured from one single acquisition are given as inputs to the algorithm of FIG. 7. The three sharpness values are those obtained for each of the three focal point by the simulation. The output of the algorithm of FIG. 7 is a prediction of depth position, which may be described as a depth estimation. The output position may be the depth for which the PDF presents its maximum value.

FIG. 7 is a flow chart which is representative of a process of determining a position of a target from sharpness. The process of FIG. 7 is performed using multiple sharpness values from a single acquisition, which have been obtained by beamforming the data from that acquisition with different focal points.

At stage 110, the process of FIG. 7 receives a set of three sharpness values as input. The three sharpness values have been obtained from a single set of ultrasound data by beamforming the data with three different receive foci (as described above with reference to stages 54a, 54b, 54c and 56).

At stage 112, a maximum likelihood estimator algorithm is used to determine a value of z from the three sharpness values that were input at stage 110.

Since the sharpness calculations for each receive focus do not depend on each other, the probability for the set of N sharpness measurements for all receive foci when a point source is located at z can be expressed as:

$$L(S_1, S_2, \ldots, S_N | z) = \Pi_{j=1}^{N} P(S_j | z) \quad \text{(Equation 5)}$$

where L is the likelihood for the set of sharpness measurements $S_1$, $S_2$, $S_N$ and N is the number of receive foci used. The PDFs, $P(S_j|z)$, have been determined using the process of FIG. 3.

The maximum likelihood estimator of the point depth, z, is the value of z for which L is maximised given an actual dataset $S_1, S_2, \ldots, S_N$ and the calibration PDFs, $P(S_j|z)$. The three sharpness values that were input at stage 110 are used as input for any suitable maximum likelihood estimator, to maximise the likelihood L as defined in Equation 5.

At stage 114, the process returns the value of z for which L is maximised. The value of Z for which L is maximised may be described as an estimated depth. The estimated depth is compared with the actual depth that is already known since the movement of the point is determined by the simulation setup.

Since the sharpness values are interpolated, the z step is modulated accordingly and divided by 1000, taking the value of 0.1 μm. The S-curves and variances were interpolated at stage 72 so that a value for each S-curve and variance is available at steps of 0.1 μm despite only having been calculated at steps of 0.1 mm in depth. The maximum of each PDF will correspond to a depth position of the updated depth vector using the new z step (in which steps of 0.1 μm are used). As a result, the error of the estimated depth may be in the order of a tenth of a micron.

The process of FIG. 7 is repeated for each set of simulated data. For each set of simulated data, the multiple sharpness values obtained by beamforming at multiple focal points are used to determine the depth of the target point (without using the knowledge of the depth of the target point from the simulation setup).

Depth estimations for all 151 datasets (all 151 particle positions) are extracted and then compared with ground truth (the scatterer positions for which the simulation was performed).

In FIG. 6, the three mean S-curves are plotted over displacement. It may be seen that, for z positions around the central point of 40 mm, each set of three sharpness values may be used to uniquely identify a z position.

In the simulation illustrated, the uncertainty introduced in the Field II simulation was relatively high. There is some oscillation in the S-curves as a result of the relatively high uncertainty. In some experimental data and/or in simulation data using a lower uncertainty, no oscillation or a low level of oscillation may be present in the S-curves (for example, see the experimental S-curves described below with reference to FIGS. 13 and 14, for which no oscillation was noticed).

Figure 8:
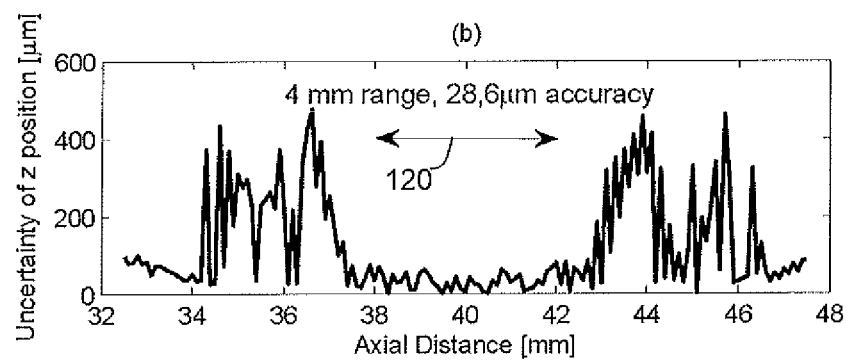
FIG. 8 is a plot of accuracy versus axial displacement.

The absolute difference between the estimated point value (estimated using the maximum likelihood estimator of FIG. 7) and the real point position (as set in the simulation) is plotted in FIG. 8. The actual position of the point target is known because it is defined when creating the phantoms. The absolute difference between the estimated and real point position may be considered to be representative of the accuracy of the proposed method.

A central region of FIG. 8 of approximately 4 mm (from 38 mm to 42 mm) is indicated by arrow 120. In this central region, the localization error (the difference between the estimated and real point position) is 28.6 μm. A value of 28.6 μm is nearly an order of magnitude lower than the wavelength in the simulation, which is 220 μm.

The accuracy is higher for the displacement region that is around the peaks of the S-curves than for regions of displacement that are not around the peaks of the S-curves.

From the simulated data, the algorithm does not appear to provide accurate estimates around both ends of the target's displacement in z (for example for positions above 43 mm or below 37 mm). A reason for the difference in accuracy may be that, for positions at the ends of the displacement, such as above 43 mm or above 37 mm in the present example, there may not be a significant difference between two neighbouring sharpness values. There may be only a small difference between the sharpness values of two curves, or between the sharpness values of all three curves. A more substantial difference between the sharpness values of the curves may allow the position of the scatterer to be better determined, and may allow for better performance of the method.

Three or more simultaneous sharpness values may be extracted for each depth position of a moving target. Those values plotted together form the sharpness curves from which a high accuracy estimate of all those positions may be extracted. The depth resolution achieved reaches 28.6 μm (0.13λ) for a 4 mm range of the total point displacement.

Using the simulation, it is demonstrated that sub-diffraction limit axial resolution for point sources may be obtained. An ultrasound imaging technique providing sub-diffraction-limit axial resolution for point sources has been proposed. It is based on simultaneously acquired multi-focal data from the same object, and on the metric of sharpness. A linear array probe is used to scan a point scatterer phantom that moves in depth with a controlled step. From the beamformed responses of each scatterer position the image sharpness is assessed. Values from all positions plotted together form a curve that peaks at the receive focus, which is set during the beamforming. Selection of three different receive foci for each acquired dataset will result in the generation of three overlapping sharpness curves. A set of three curves combined with the use of a maximum-likelihood algorithm may then be able to estimate with high precision each depth location. Estimated values are compared with ground truth, demonstrating that an accuracy of 28.6 μm (0.13λ) is achieved for a 4 mm range around the peaks of the curves.

The simulation above is described with reference to three focal points, and hence three S-curves. A greater number of S-curves may be used. For example, a number of overlapping S-curves may be used that covers axially a whole image. For example, for an image that extends from 20 mm to 60 mm axially, an S-curve may be calculated for focal points at 2 mm intervals across a range from 20 mm to 60 mm, or from 22 mm to 58 mm. Any suitable increment in focal point position may be used. The S-curves may be determined for focal points that are positioned such that, for every axial position in the desired image, there are at least two (or more) S-curves that have distinctly different values for the sharpness of that axial position.

Increasing the number of overlapping S-curves (for example, by beamforming the signals with a greater number of focal points) may increase the range of positions for which position determination may be provided with high resolution. Increasing the number of overlapping S-curves may increase the high-resolution range and/or reduce the uncertainty of the position estimates.

A single signal dataset (or image) may be characterised by a set of several sharpness values. In ultrasound, all of the sharpness values may be obtained from the same initial data set. It may be straightforward to obtain several sharpness values for a given data set since the receive data may be beamformed accordingly. Any desired number of sharpness values may be obtained from the same data. Any number of S-curves may be formed. The same calibration data may be used to form different S-curves.

In this simulation, the variance extracted from the simulated ultrasound data is only based on the addition of noise to the raw signals. In other simulations or embodiments, a different fit (for example, not a Lorentzian fit) may be used. An alternative way to produce interpolated mean S-curves and extract statistical measures may be adopted.

A calibration method may be generated in order to address the particle location. The method of FIGS. 3 and/or 7 may be modified for use in a real tissue environment where strong aberrations may provide a variable and unpredictable point spread function.

Figure 9:
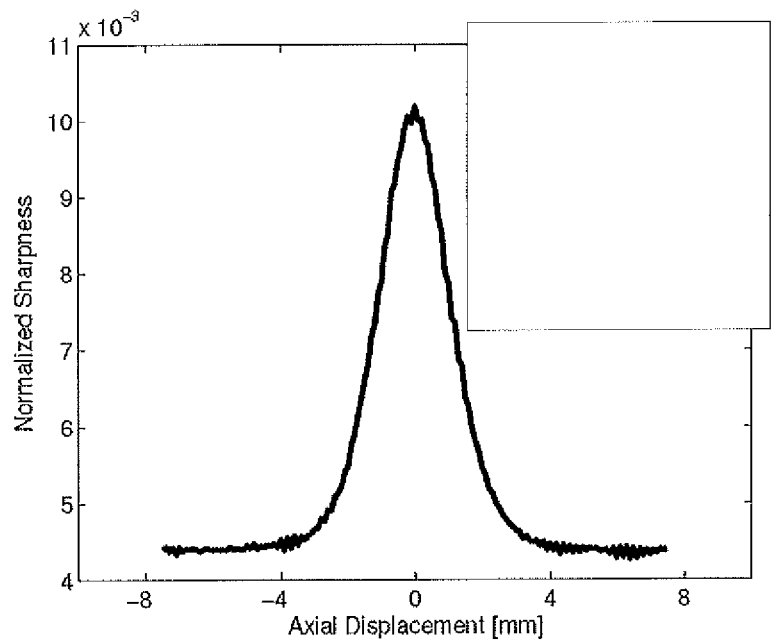
FIG. 9 is a plot of sharpness as a function of displacement.
Figure 10:
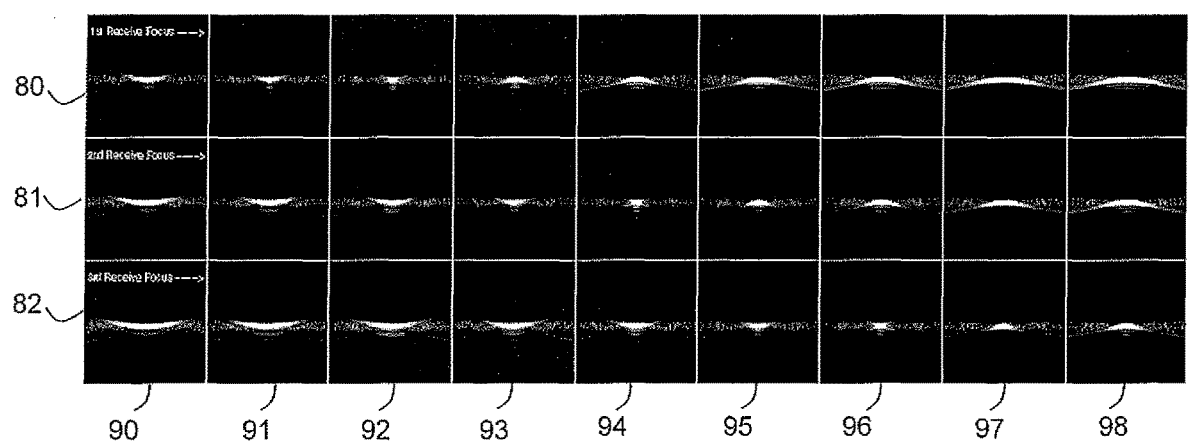
FIG. 10 is a set of images of a point target.

FIGS. 9 and 10 show additional data derived from Field II simulations. FIG. 9 shows normalized sharpness plotted over axial displacement for a Field II simulated point target, moving across the z-axis (depth). In this example, each sharpness value is assessed in every position, and all the values plotted together create a sharpness curve (S-curve). Sharpness takes higher values as the point source moves closer to an initial position where the focus is located, and decreases again when moving away from it.

FIG. 10 shows the PSFs of a single point scatterer as a function of point displacement. A point target is imaged as a function of axial displacement from an initial position (0 mm, represented by column 94). Each image corresponds to an area of 10 mm×10 mm. The same dataset has been beamformed with three different foci in receive, with a 2 mm separation between each two foci. Rows 80, 81 and 82 are representative of first, second and third foci. Columns 90 to 98 are representative of displacement of the target in 1 mm increments from −4 mm to 4 mm. A 60 dB dynamic range display is used. It may be seen that for each row, the target is best focused when the position of the target coincides with the position of the focal point.

The flowcharts of FIGS. 3 and 7 have been described above in the context of simulation. An experiment has also been performed in which multiple sharpness values from a single set of ultrasound data are used to determine the depth of a target.

Figure 11:
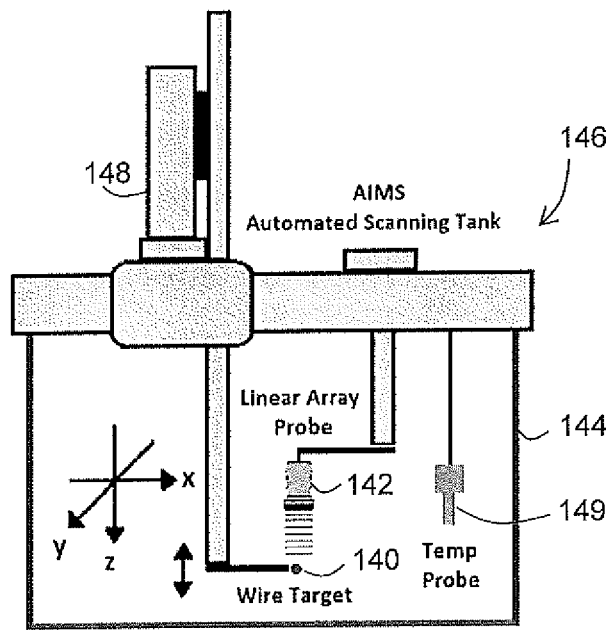
FIG. 11 is a schematic diagram of a calibration apparatus.

An apparatus used to perform calibration is illustrated in FIG. 11. The apparatus comprises an AIMS automated scanning tank 146. The automated scanning tank 146 comprises a tank 144 that is filled with water. A wire target 140, which is representative of a point source, is inserted into the scanning tank 144. The wire target 140 may be positioned in x, y and z coordinates (as indicated in FIG. 11) by positioner 148. Positioning of the wire target 140 is controlled by a control processor (not shown).

A linear array probe 142 is mounted in the tank 144 and may be positioned by a further positioner. In operation, the linear array probe 142 is used to scan the wire target 140. The wire target 140 is moved from an initial position across the z dimension and is imaged for every displacement.

In the present embodiment, the linear array probe 142 is a 7 MHz, 192 element linear array transducer. In this particular case, the linear array is a 7 MHz BK8804 transducer. In other embodiments, any suitable transducer may be used. The transducer may be, for example, a linear array or 2D array. Any suitable ultrasound frequency may be used, for example any frequency between 1 and 18 MHz.

A temperature probe 149 monitors the temperature of the water in the tank 144.

The wire target 140 is a custom single-wire phantom. The diameter of the wire is 0.07 mm.

The wire target 140 has the ability to be moved in all directions with accuracy, using the positioner 148. In the experiment, the x and y coordinates of the wire target 140 are kept fixed. The initial z position of the wire target 140 is at 40 mm from the surface of the transducer 142 and the wire target 140 is moved to other z positions. In other embodiments, the wire target 140 may be moved in x and/or y and/or x coordinates.

The transducer 142 is connected an ultrasound scanner (not shown). In the present embodiment, the ultrasound scanner is the 1024 channel experimental ultrasound scanner SARUS (Synthetic Aperture Real-time Ultrasound System). Measurements are performed using SARUS. Matlab scripts are used for data post-processing.

Figure 12:
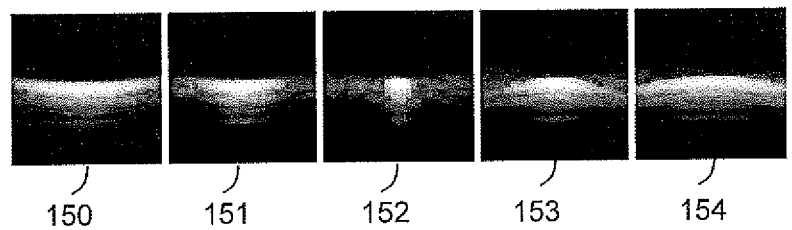
FIG. 12 is a set of images of a point target.

FIG. 12 shows PSFs (150 to 154) corresponding to maximum, minimum and zero displacements for both ends of the range of movement. Image 150 is representative of maximum negative displacement (−7.5 mm or a depth of 32.5 mm). Image 151 is representative of a displacement of −7.5/2. Image 152 is representative of 0 displacement. Image 153 is representative of a displacement of +7.5/2. Image 154 is representative of a displacement of +7.5 mm (which is the maximum positive displacement at 47.5 mm depth). Each image includes an area of 6 mm×6 mm and a 60 dB dynamic range is used. The SARUS scanner is used for all acquisitions.

The speed of sound in the tank is measured to be c=1484 m/s. The wavelength used is 212 µm. The z step by which the wire target 140 is moved between successive emissions is 108.7 µm. The focuses used are 38 mm, 40 mm and 42 mm. Other experimental setup parameters are the same as provided in Table 1. In other embodiments, any suitable values for each of the parameters may be used.

To perform a calibration for a particular focal point (for example, a focal point at 40 mm), the phantom wire target 140 is moved to a succession of positions in an axial (z) direction, and data for each of the axial positions is beamformed with a focus at the particular focal point. A sharpness value is obtained for the beamformed data at each axial position.

In practice, the calibration for several focal points may be performed from one set of positions of the phantom, since sharpness values for multiple focal points may be obtained from each set of ultrasound data.

A method of calibration using the apparatus of FIG. 11 is described with reference to the flow chart of FIG. 3. The transducer 142 is used to scan the custom single-wire phantom positioned inside the scanning tank 144.

At stage 50 of FIG. 3, the wire target 140 is positioned at an initial position. In the present embodiment, the initial position is z=40 mm. The x and y coordinates remain at (0,0) throughout the process of FIG. 3.

At stage 52, a single unfocussed plane wave emission is transmitted by the transducer 142 towards the wire target 140. Transmission of ultrasound is performed through a single plane wave using all the transducer elements as the transmitting aperture. Reflected ultrasound signals are received by each element of the transducer 142. The signals received by each element of the transducer are amplified, digitized by an ADC 12 and stored in a memory 16 as a set of ultrasound data. Raw ultrasound data from the single unfocussed emission is acquired from all 192 channels (192 transducer elements) individually in receive. In this experiment, the sampling frequency is 70 MHz. In other embodiments, any appropriate sampling frequency may be used.

After emission the data are stored. Although in the present embodiment, sharpness values are calculated after each emission, in other embodiments data from multiple emissions may be stored and some or all of the data may be beamformed after all the emissions and data acquisitions have been performed.

In ultrasonics, it is common to utilize the focus in receive as the element signals can be stored after the transmission, and beamformed offline in multiple ways. A standard way to process the received transducer element signals is the Delay-and-Sum (DAS) beamformer as used in this embodiment. However, in other embodiments any other appropriate beamformer may be used. Data may be beamformed offline at any time after the acquisition of the data.

At stage 54a, the ultrasound data is beamformed at a focal point of (x, y, z)=(0, 0, 38 mm). At stage 54b, the ultrasound data is beamformed at a focal point of (x, y, z)=(0, 0, 40 mm). At stage 54c, the ultrasound data is beamformed at a focal point of (x, y, z)=(0, 0, 42 mm). The signals are time-delayed, weighted and subsequently summed to form the maximized beamformer output B(t) as given in Equation 2.

In other embodiments, different focal points may be used. The focal points may differ from each other in x and/or y coordinates in addition to, or instead of, differing in z coordinate.

The data resulting from each beamforming step comprises a plurality of samples. An envelope detection (in this case, a Hilbert transform) is performed for each sample. In other embodiments, a different envelope detection may be used. The output of the envelope detection is an amplitude for each of the samples.

Sharpness is derived from the amplitudes of the received transducer elements after the Hilbert transform, i.e. envelope detection, is performed. By determining sharpness using the amplitudes of the beamformed signals rather than by using pixel intensities of an image, distortions from image format conversions may be avoided.

At stage 56, the processor 14 selects a region around the wire target 140 for which to calculate sharpness. (In the present calibration method, the position of the wire target 40 is known and the region is selected based on the known position.) For each set of beamformed data (one for each focal point), the processor 14 calculates a sharpness value using Equation 3 for the samples within the selected region. The output of stage 56 is the three calculated sharpness values.

At stage 58, the control processor determines whether there are axial positions for which measurements have not yet been made. At stage 60 the wire target is moved to the next location in the axial direction using the AIMS III positioning setup. The control processor controls the positioner 148 to move the wire target 140 by 108.7 µm to the next location, which is at z=40.1087 mm.

The positioning setup including positioner 148 has a minimum movement step equal to 1/92 mm=10.87 µm. The ratio 1/92 is attributed to a stepper motor system that is used to position the wire target 140 in the tank 144. The stepper motors drive the positioner 148 through reducing gear heads, which rotate pinions against a precision rack. The resulting position resolution is thus at maximum 10.87 µm, but may take lower value (higher precision).

In the present embodiment, the z axis step that is used is 10 times the minimum z axis step, hence 108.7 µm. In other embodiments, any integer multiple of the minimum z axis step may be used. Different positioners may be used. The minimum z step may be of a different size. In the present embodiment, it is found that the positioner 148, if moved up and down with the required z step several times, returns to the initial position with nanometric accuracy.

Once the wire target 140 has been repositioned at z=40.1087 mm, stages 52 to 60 are repeated. Stages 52 to 60 are repeated with z increasing by 108.7 µm each time until a position of 47.5 is reached. Stages 52 to 60 are then repeated with decreasing values of z from 40 mm to 32.5 mm.

In all, stages 52 to 58 are repeated for 139 steps, i.e. 139 different z positions, each separated by a step of 108.7 µm.

At stage 62, sharpness curves are determined for each of the three focal points using the data from the 139 position steps. In alternative embodiments, no sharpness curves are determined at stage 62, and the sharpness values generated at stage 56 are used directly to generate the mean sharpness curves at stage 68 as described below.

At stage 64, the control processor determines whether more frames are required. In the present embodiment, the moving of the wire target 140 through the 139 z positions is performed 10 times in total to provide statistical data. Therefore at the first instance of stage 64, the process passes to stage 66 (repeat process) and then iterates through stages 50 to 64 as described above for 9 additional times. In other embodiments, any number of repetitions may be used. The repeated data may be used to provide an error assessment so that the accuracy of a position estimation for the wire target is determined.

10 frames are acquired for each position of the wire target 10 and as a consequence 10 S-curves can be formed for each receive focus. From the multiple frames it is possible to extract the S-curves and their associated variance.

At stage 68, the processor 14 extracts a mean S-curve for the 10 frames. At stage 70, the processor 14 extracts a standard deviation for the data from the 10 frames. The Lorentzian function may be a good approximation of an S-curve peak. The standard deviation has higher values around the peak of a curve and lower at the edges.

Figure 13:
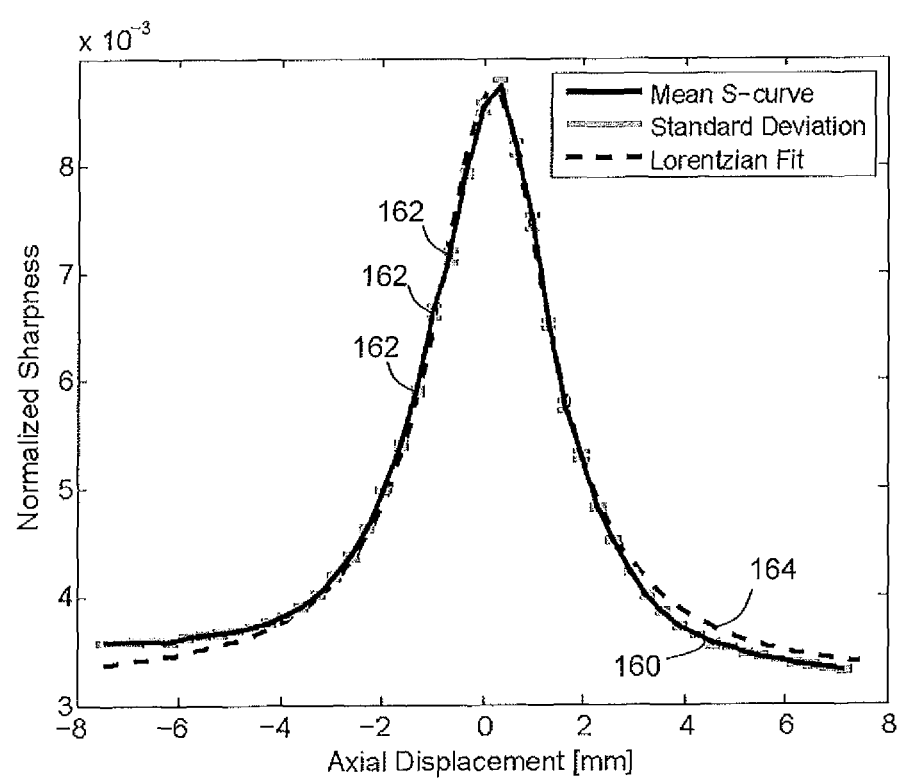
FIG. 13 is a plot of a sharpness curve with Lorentzian fit and standard deviation.

FIG. 13 is a plot of a mean S-curve 160 for a single focal point (derived from repeated measurements). A standard deviation 162 is provided at each of a selected set of points. Position is shown as axial displacement in millimetres relative to the receive focus. For this curve, the receive focus is at z=40 mm. Therefore the zero of displacement is at z=40 mm. A Lorentzian function 164 has been fitted to the mean &-curve. The peak of the curve is located at the position of the receive focus.

Figure 14:
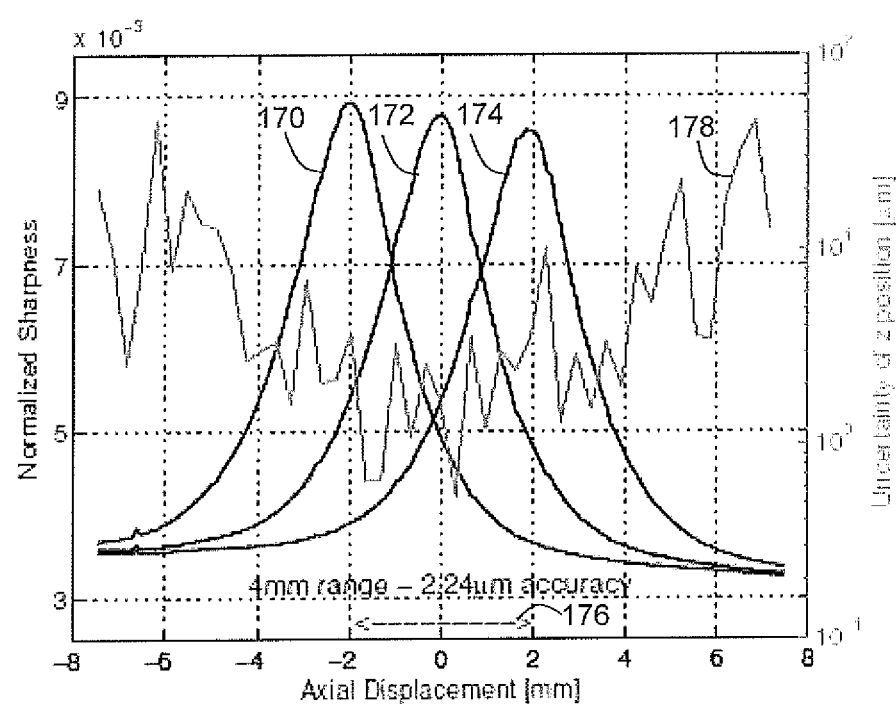
FIG. 14 is a plot of three sharpness curves, overlaid with a plot of accuracy of z position.

FIG. 14 shows a set of three S-curves 170, 172, 174 that are obtained from data for a wire target 140 moving in depth. The data from which the S-curves are generated are acquired using the SARUS scanner. Each of the S-curves 170, 172, 174 is obtained from the same ultrasound data from a single ultrasound transmission. Each curve is obtained after beamforming the same ultrasound data with a different focus in receive. Curve 170 is obtained for a focal point at z=38 mm. Curve 172 is obtained for a focal point at z=40 mm. Curve 174 is obtained for a focal point at z=42 mm. Axial displacement is indicated relative to z=40 mm.

It may be seen that for each focal point, the sharpness value peaks when the wire target 140 is located at the focal point. It may be expected that sharpness value will peak when the target is at the focal point, since sharpness value may be used as a measure of focus.

The mean S-curves generated at stage 68 (one mean S-curve for each focal point) and the standard deviations calculated at stage 70 are used as inputs to stage 72. At stage 72 the processor interpolates the mean sharpness values and standard deviations, which were originally obtained for 139 z positions, to a larger number of z positions. In the present embodiment, the statistical measures (mean sharpness values and standard deviations) are interpolated by a factor of 1000 using the Matlab spline interpolation function. In other embodiments, any interpolation factor and/or method of interpolation may be used.

At stage 74, the processor 14 inserts the interpolated mean S-curve and interpolated standard deviation into Equation 4 to determine PDFs for each of the focal points.

In the simulation described above, a Lorentzian fit of the mean S-curve and variance was used in the determination of the PDFs. In the experiment now described, an interpolated version of the mean and variance data is used in the determination of the PDF, instead of using an interpolated version of the Lorentzian. $\overline{S}_j(z)$ in Equation 4 now represents the interpolated mean S-curve for the jth focal point. $\overline{\sigma}_j^2$ represents the interpolated variance for the jth focal point. As the Lorentzian fit may not be a perfect match to the mean and variance curves, using an interpolated version of the mean and variance curves rather than an interpolated version of the Lorentzian fits may result in improved accuracy.

In different embodiments, a different equation for PDF may be used, or a different calibration function other than PDF may be used to relate value of sharpness to position. Any suitable statistical measure may be used instead of or in addition to mean, standard deviation or variance.

At stage 76, the PDFs are output and/or stored in memory 16. In further embodiments, any suitable functions derived from the data from the different focal points may be used.

Once the PDFs have been determined, a maximum likelihood estimator is used to determine positions for the target in each data set using only the sharpness values for the different focal points (and without using the known position of the target). The z positions estimated using the maximum likelihood estimator are compared to the actual z positions that are known from the positioning process using the positioner (since in the experiment the movement of the wire target 140 is determined by a controlled step). The true positions of the wire target 140 are known due to the high precision positioning system.

The maximum likelihood estimation is performed for each of the 139 z positions. Depth estimates for 139 ultrasound data sets (corresponding to 139 wire target positions) are calculated and compared with the positions from the positioner, which may considered to represent ground truth. The method aims to provide a precise estimate of each point source position. The estimate may be considered to be unique since each position may be characterized by three distinct sharpness values.

Since the sharpness values are interpolated, the z step is modulated accordingly and divided by 1000, taking the value of 108.7 nm. The maximum of each PDF will correspond to a depth position of the updated depth vector using the new z step. As a result, the error of the estimated depth may be limited approximately the order of a tenth of a micron.

FIG. 14 also shows absolute difference between estimated and real wire position (line 178), as determined by experiment as described above. It is found that the method of position estimation does not perform uniformly for the entire 15 mm distance (the 15 mm range in z over which the wire target 140 is moved). It may be the case that estimates around both ends of the wire displacement should not be taken into account.

The uncertainty of x position when the area of interest is narrowed down to 8 mm around the zero point of the graph (wire target at z=40 mm) reaches a value of 3.05 μm. The highest accuracy of 2.24 μm (around 0.01λ) is noticed for a 4 mm range around the zero point. The 4 mm range is around the crossover points of the S-curves, as shown by arrow 176 in FIG. 14.

It is shown that in some circumstances an axial resolution almost equal to λ/100 may be obtained using a position determination method as described with reference to FIGS. 3 and 7.

It is shown that PSF-based localization methods, with the use of sharpness, may be applied to ultrasound data for super-resolution, sub-diffraction localization imaging. Micrometric depth resolution may be obtained.

In order to quantify a depth resolution improvement that may be achieved by the sharpness methodology, a system axial resolution is assessed.

Figure 15:
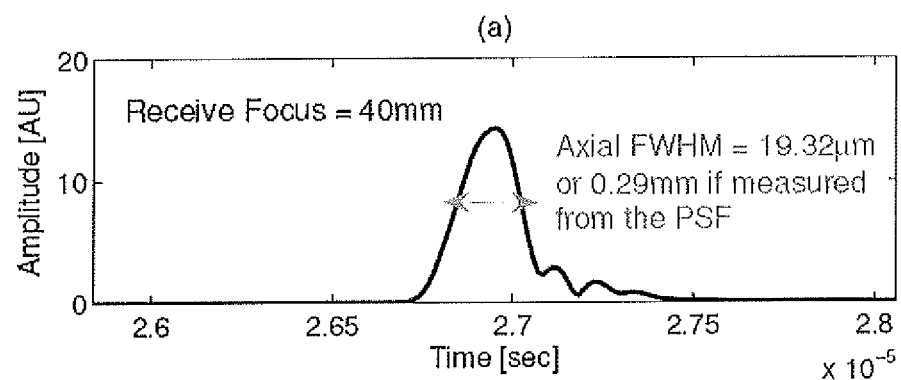
FIG. 15 is a plot of axial FWHM assessment from an RF signal.
Figure 16:
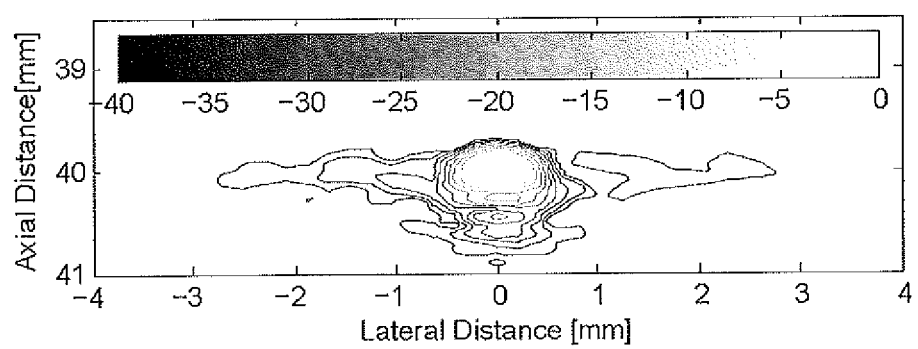
FIG. 16 is a plot of axial FWHM assessment from a point spread function.

FIGS. 15 and 16 show how an axial Full-Width at Half-Maximum (FWHM) is extracted from the RF data received by the ultrasound transducer and from the contour plot of the PSF illustrated in the middle plot of FIG. 16. The extraction of the FWHM from the RF data is shown in FIG. 15 and the extraction of the FWHM from the PSF is shown in FIG. 16. For FIG. 16, a 40 dB dynamic range display is selected as the width of the main lobe is of major interest. The data shown for each figure is obtained with the wire target 140 positioned at z=40 mm.

In FIG. 15, the axial FWHM is measured from the RF signal that passes through the centre of the wire target. The Hilbert transform has been first employed, resulting in a Gaussian-shaped curve from which a value of 19.32 μsec is calculated.

In FIG. 16, all Hilbert data undergo logarithmic compression before display and the FWHM corresponds to the −6 dB decrease that is equal to 0.29 mm. With the speed of sound being constant, there is no difference between these two values.

From the FWHM it is possible to calculate the standard deviation that for a Gaussian function is given by:

$$FMHM = 2\sqrt{2\ln 2}\sigma \approx 2.355\sigma \qquad \text{(Equation 6)}$$

resulting in a value equal to 121.5 μm=0.57λ.

The same FWHM calculation is repeated for all 139 experimental datasets. In contrast to the lateral FWHM that is subject to the focus and may change greatly with axial displacement, the axial FWHM, and the standard deviation as a consequence, remain almost unchanged throughout the displacement.

Figure 17:
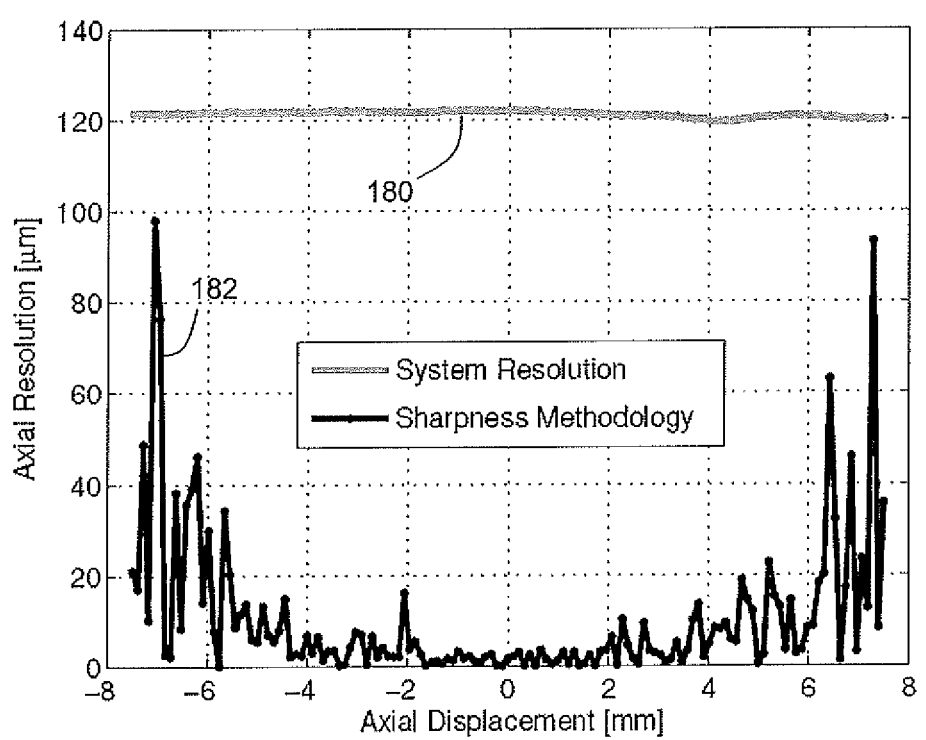
FIG. 17 is a plot of system axial resolution compared with axial resolution obtained using a sharpness methodology.

In FIG. 17, the standard deviation obtained from the FWHM, which may represent the system axial resolution, is compared to the depth localization accuracy of the proposed method. Line 180 is the system axial resolution, which remains fairly constant with z position. Line 182 is the resolution obtained using the sharpness methodology.

The sharpness method describes above may provide superior resolution (compared to the system resolution) for the whole wire displacement but may become optimal for a 4 mm region around the initial position. This region is equal to two times the distance between two successive receive foci. The optimal region around the initial position may be due to the fact that the rate of change between neighbouring sharpness values.

To increase the super-resolution range, the number of overlapping S-curves may be increased. For example, the number of overlapping S-curves may be increased until they cover axially an entire image. A single image may then be characterized by a set of several sharpness values. The number of S-curves used may be unlimited. A single set of data may be beamformed with any number of foci. By using a large number of S-curves, high resolution may be achieved over a substantial region of an image. In some circumstances, high resolution may be achieved over a whole image.

The experimental method of position determination described above may achieve micrometre depth resolution in medical ultrasound. The approach is based on a simple aberration dependent sharpness metric of a single point emitter. A linear transducer is used to scan a single-wire phantom, as a good point source approximation, which is placed in a setup with a high precision positioning system. The wire is moved around an initial depth of 40 mm with a controlled z-step and all acquired data are stored before moving to the next position. The localization of a point source may rely on the generation of three overlapping sharpness curves. This may be managed by deploying three respective receive foci and by assessing the sharpness values, the integrated square intensity over the emitter, after each acquisition as a function of depth. Each curve peaks at the receive focus and this may enable a unique position of the point source to be identified. By using a maximum likelihood algorithm with a calibration standard, sharpness may be able to provide an estimate of each depth position with an accuracy of 2.24 μm (≅0.01λ) for a range of 4 mm around the peaks of the curves.

In other embodiments, similar methods may be used to estimate movement in all coordinates. Positions determined using the position determination method described above may be used as an input to particle tracking applications.

Although the method of FIGS. 3 and 7 is described above with reference first to simulated data and then to experimental data in which a wire target 140 is used as a point source, the method of FIGS. 3 and 7 may in practice be used for the detection of any target that may be considered as a point source. One example of a target that may be considered as a point source is a contrast microbubble. Contrast microbubbles are used to provide contrast in ultrasound images, particularly in medical ultrasound images.

In one embodiment, the method of FIG. 3, or a similar method, is used to perform a calibration for a contrast microbubble target.

The non-linear behaviour of microbubbles may be simulated. Differential equations are known that describe bubble oscillation. For an experiment, a number of wires may be put across the axial movement of the bubbles in order to have a precise description of the actual depth.

Probability density functions are obtained for each of a plurality of focal points are obtained. The probability density functions are used in determining the position of contrast microbubbles at unknown depths. Although the determination of position in depth is described in this embodiment, in other embodiments a lateral position may be determined instead of or in addition to a position in depth. The lateral position may be determined using the method of FIG. 7 or by any other method of position determination, for example any other method of super-resolution position determination.

A position determination method is performed as followed. Contrast microbubbles are introduced into an area of interest. In the present embodiment the microbubbles are Sonovue® microbubbles, which are sulphur hexafluoride bubbles with phospholipidic monolayer shells. In other embodiments, any microbubbles may be used.

In this embodiment, the contrast microbubbles are introduced into the blood vessels of a patient. In other embodiments, the area of interest may comprise any suitable area, volume or structure. The area of interest may comprise tissue of any part of the human or animal body.

Contrast microbubbles are designed to produce strong reflections in ultrasound. Each contrast microbubble may be considered to be a point source.

A transducer 10 transmits ultrasound energy towards the structure of interest, for example towards the blood vessels into which the contrast microbubbles have been introduced.

In the present embodiment, a single plane wave is transmitted. The plane wave is an unfocussed beam.

An ultrasound pulse is used that has been designed for detection of microbubbles. The ultrasound pulse uses a pulsing strategy that enables the subtraction of background tissue echoes. The ultrasound pulse may be such that a linear response may substantially cancel the pulse. However, microbubbles have a non-linear response. Therefore, echoes from microbubbles may be received while substantially removing echoes from tissue.

Ultrasound energy is reflected from each of the contrast microbubbles. In the discussion below, we consider only one of the contrast microbubbles. However, the method described may be used to determine the position of many microbubbles. In some circumstances, the effectiveness of the position determination may depend on the density of the microbubbles. For example, the position determination for each of the microbubbles may be more accurate when the microbubbles are well separated. It may be necessary to control the microbubble density in an image, as each sharpness value may be evaluated only from a small box around a single PSF. Within such a limit, aberrations may be well-defined and symmetric and may be contained within a single analysis frame.

Considering a single microbubble target, each element of the transducer 10 receives a respective ultrasound signal which has been reflected from the microbubble target. The received ultrasound signals are digitized by the ADC 12 and stored in the memory 16.

The processor 14 beamforms the received ultrasound data with each of a plurality of focal points. A Hilbert transform is performed to obtain an envelope of the received transducer signals. In the present embodiment, a Delay-and-Sum beamformer is used. In other embodiments, any appropriate beamformer may be used. Three sets of beamformed data are output, each beamformed with a different focal point.

The processor 14 evaluates a sharpness value for each set of beamformed data. In order to evaluate the sharpness value, the processor 14 determines a region from which the sharpness value will be evaluated.

In the present embodiment, the processor 14 determines an approximate position for the target by determining the sample that has a maximum amplitude value (for example, a global or local maximum amplitude). The processor 14 selects a square region of a given size around the maximum amplitude sample. In other embodiments, the processor 14 may detect one or more point spread functions. In further embodiments, any appropriate method of region selection may be used. The selected region may be of any appropriate shape (for example, square, rectangle or circle) and of any appropriate size. The size of the region may be obtained so as to have enough samples to perform an adequate sharpness calculation.

In some embodiments, the processor 14 determines statistics of data points within the region. For example, the processor 14 may determine a range of amplitudes or a distribution of amplitudes. The processor 14 may change the size and/or position of the region in response to the determined statistics. For example, if the determined statistics indicate that more than one target is present in the selected region, the processor 14 may reduce the size of the selected region until the statistics show that it contains only one target.

The processor evaluates the sharpness value for each set of beamformed data by using Equation 3 to calculate a normalised sharpness value for the samples in the selected region. The number of sharpness values obtained is the number of different focal points used.

The processor 14 uses a maximum likelihood algorithm to determine the most likely depth of the target from the multiple sharpness values. The maximum likelihood algorithm uses the PDFs that have been obtained from calibration.

The maximum likelihood estimator maximises likelihood L of Equation 5. Any suitable maximum likelihood estimator may be used to maximise the likelihood. The maximum likelihood estimator returns an estimate for the position of the target in the z direction. If there are multiple microbubbles present in the area of interest, a region may be selected around each of the microbubbles. For example, an approximate position of each microbubble may be determined by finding local maxima in amplitude. A region may be selected around each local maximum. A set of sharpness values may be determined for each of the selected regions.

Once the position of each microbubble has been determined, the positions may be used to form images or to obtain further information about the area of interest. For example, positions of microbubbles may be used to perform tracking.

By using a position determination method based on a sharpness metric (or another suitable metric), positions of microbubbles or other point sources may be determined with a resolution beyond the diffraction limit. High resolution position determination may be of use in many medical applications, for example in imaging of small structures such as microvessels. Position may be determined for any suitable sources, for example any suitable point sources. In one example, the source may be a tumour. Position may be determined for particle tracking and/or for tracking of any appropriate anatomical feature.

Position may be determined at high resolution from a single ultrasound transmission by beamforming a single set of ultrasound signals using multiple foci. Multiple sets of beamformed data may be used to obtain multiple sharpness values for a target and hence a high-resolution position for that target.

By obtaining multiple sets of beamformed data from a single set of received ultrasound signals, super-resolution imaging may be obtained without requiring the use of additional ultrasound transmissions. In some circumstances, the position determination method described may provide a fast and/or efficient method of obtaining high-resolution position data.

The number and spacing of foci may be chosen to give high resolution over a desired range. Closely spaced foci may result in higher resolution than more widely spaced foci. A set of foci that cover a wider range of z may achieve a greater high-resolution range than a set of foci that cover a narrower range in z. Since the different foci are achieved through beamforming of the same ultrasound data, there may be no limit on the number or position of foci that may be used.

In the embodiments described above, plane wave transmission is chosen. Plane wave transmission may offer fast acquisitions and one emission may be able to provide all the necessary information for the algorithm. However, in other embodiments, Synthetic Aperture ultrasound may be used. The low-resolution images acquired from single SA emissions may provide an even higher frame rate, increasing the amount of collected data.

In some embodiments, for example for targets that are located at greater depths at which a lower Signal-to-Noise Ratio might compromise the performance of the method, conventional focussed ultrasound may be adopted. The transmit focus may be positioned far from the transducer's surface. In such a case, a higher number of emissions may be required, increasing the time needed between two successive RF data acquisitions.

The acquisition time, the depth of interest and the velocity of a moving particle may introduce complexity in the choice of parameters as given in Table 1. Any of the parameters may be modified as needed.

In the embodiments described above, beamforming is performed on stored data and may be performed after all acquisitions have taken place. In other embodiments, beamforming may be performed directly after each acquisition. Beamforming may be performed by an ultrasound imaging apparatus while ultrasound images are being acquired.

The embodiments described above describe the use of a linear array transducer. In other embodiments, a 2D array transducer may be used. Ultrasound scanning with 2D array probes may be exploited to extract sharpness values that may correspond to a total position instead of just to a z position. Position may be determined in at least one lateral dimension.

Modern 2D arrays exist in which transducer elements are not located in one row only (for example, 1×192 elements) but have dimensions such as, for example, 32×32 elements. When such an array is used, received signals may provide information about the whole position of a scatterer. The position information may not be restricted to x and z position. A measured sharpness may then correspond to a full position and not a z only coordinate.

The number of S curves is not limited (any number of S-curves may be obtained from the same data). Therefore, it may be possible to have as many curves as required for the estimation of 3 position parameters (x, y and z) instead of one parameter (z).

Any suitable metric may be used to perform the position determination method. The metric may be any sharpness metric. The metric may be any metric that relates to position and/or focus, for example a metric that measures or depends on contrast or intensity. The value returned by the metric should be different for different foci.

In embodiments, any suitable statistical measures may be used. A different definition of PDF may be used from that described above, or a function other than PDF may be used. Any calibration function may be used by which a position may be determined from values of the metric. The calibration function may also return a probability or likelihood associated with the determined position.

In the embodiments above, sharpness is determined from raw ultrasound data. In further embodiments, a value of a metric (for example, sharpness) may be obtained from image data that has been obtained from ultrasound signals. Multiple images may be obtained by beamforming a set of ultrasound data using multiple foci, and a value for the metric may be determined from each of the images.

It may be understood that the present invention has been described above purely by way of example, and that modifications of detail can be made within the scope of the invention.

Each feature disclosed in the description and (where appropriate) the claims and drawings may be provided independently or in any appropriate combination.

What is claimed is:

1. A method of determining a position of a target object using a sharpness metric and using a position calibration determined for at least one further real or simulated object, the method comprising:

receiving a set of ultrasound signals comprising a plurality of ultrasound signals representative of ultrasound energy received from the target object;

for each of a plurality of different focus positions, beamforming the received set of ultrasound signals at the each focus position of the plurality of different focus positions thereby to obtain multiple sets of beamformed data from the set of ultrasound signals, and determining a value of the sharpness metric for the target using each of the sets of beamformed data thereby to determine a value of the sharpness metric for each of the plurality of different focus positions;

receiving or determining a set of position calibrations, wherein each calibration of the set of position calibrations is determined for a different position of a plurality of known calibration positions of at least one further real or simulated object, different to said target object, and each calibration of the set of position calibrations comprises or represents a variation of sharpness value with focus position for the position of the further real or simulated object associated with that calibration of the set of position calibrations; and calculating a position of the target object by determining variation of the values of the sharpness metric with focus position, and performing a comparison or statistical procedure between the variation of the values of the sharpness metric with focus position for the target object and variations of the values of the sharpness metric with focus position obtained from the set of position calibrations for the plurality of known positions of the at least one further real or simulated object, wherein the performing of the comparison or statistical procedure includes or represents an interpolation or other procedure performed with respect to the sharpness metric values and/or the set of position calibrations such that the position of the target is determined with an improved spatial resolution that provides an improvement with respect to a difference between adjacent calibration positions of the plurality of calibration positions and that is below a diffraction limit of the ultrasound signals, and wherein each of the plurality of different focus positions is a respective different position in an axial direction within a region around the target object, and for each of the plurality of different focus positions the determining of value of the sharpness metric for that focus position comprises determining the value of the sharpness metric for the target object using a plurality of data points of a respective set of beamformed data of the multiple sets of beamformed data, each data point corresponding to a different position in the region.

2. The method according to claim 1, wherein beamforming the ultrasound signals at the focus position comprises applying time delays to at least some of the ultrasound signals.

3. The method according to claim 2, wherein the plurality of ultrasound signals correspond to a respective plurality of ultrasound transducer elements, and the time delays are applied based on a distance from each transducer element to the focus position.

4. The method according to claim 1, wherein beamforming the ultrasound signals further comprises applying apodization weights to the ultrasound signals.

5. The method according to claim 1, wherein the set of position calibrations comprises a plurality of calibration functions, each calibration function corresponding to a respective focus position.

6. The method according to claim 5, wherein for each focus position, the corresponding calibration function is a function of position of the at least one further real or simulated object and value for the metric with that focus position.

7. The method according to claim 5, wherein each calibration function comprises a probability density function.

8. The method according to claim 5, wherein calculating the position of the target object comprises determining a position for which a likelihood of the target object being present is maximised.

9. The method according to claim 8, wherein calculating the position of the target object comprises using a maximum likelihood estimator.

10. The method according to claim 1, wherein the beamformed ultrasound signals comprise a plurality of data points, and wherein the value for sharpness metric is dependent on amplitudes for a selected at least some of the plurality of data points.

11. The method according to claim 1, further comprising selecting a region around the target object, wherein the metric is determined for the selected region.

12. The method according to claim 11, wherein selecting a region around the target object comprises determining an approximate position for the target object and selecting a region around the approximate position.

13. The method according to claim 1, wherein the beamformed ultrasound signals comprise a plurality of data points, the value for sharpness metric is dependent on amplitudes for a selected at least some of the plurality of data points, and the selected at least some of the plurality of data points are data points within the selected region.

14. The method according to claim 1, wherein the target object comprises a contrast microbubble.

15. The method according to claim 14, wherein the ultrasound signals are received from an ultrasound transmission, the ultrasound transmission comprising a non-linear ultrasound pulse.

16. The method according to claim 1, wherein the target object is part of an object to which ultrasound energy is transmitted from an ultrasound source, and the axial direction is a direction into the object from the ultrasound source.

17. The method according to claim 16, wherein the ultrasound source comprises an ultrasound transducer, the ultrasound signals are received by the ultrasound transducer, and the determined position is a position in an axial direction with respect to the ultrasound transducer.

18. The method according to claim 1, wherein at least one of the ultrasound signals or the adjusted ultrasound signals comprise ultrasound data.

19. The method according to claim 1, wherein the position calibration comprises at least one of:
   a likelihood or probability that an object in a given position will result in a given value of the sharpness metric;
   at least one probability density function; or
   at least one of sharpness curves or probability density functions from at least one of measurements or simulations of the value of the sharpness metric for an object that is placed at a plurality of positions.

20. A method of determining a position of a target using a sharpness metric, the method comprising:
   receiving a plurality of ultrasound signals representative of ultrasound energy received from the target;
   for each of a plurality of different focus positions beamforming the received ultrasound signals at the each focus position of the plurality of different focus positions, and determining a value of the sharpness metric for the target using the beamformed signals;
   receiving or determining a calibration that comprises or represents sharpness values determined for at least one further real or simulated target for a plurality of different focus positions and for a plurality of known positions of the at least one further real or simulated target; and
   calculating a position of the target by determining variation of the values of the sharpness metric with focus position, and performing a comparison or statistical procedure between the variation of the values of the sharpness metric with focus position and variations of the values of the sharpness metric with focus position obtained from the calibration for known positions of the at least one further real or simulated target,
   wherein each of the plurality of different focus positions is a respective different position in an axial direction within a region around the target, and for each of the plurality of different focus positions the determining of value of the sharpness metric for that focus position comprises determining the value of the sharpness metric for the target using a plurality of data points of the beamformed signals, each data point corresponding to a different position in the region,
   wherein the beamformed ultrasound signals comprise a plurality of data points, and wherein the value for sharpness metric is dependent on amplitudes for a selected at least some of the plurality of data points, and
   wherein the sharpness metric is calculated using the fourth power of the amplitudes of the selected at least some of the plurality of data points.

* * * * *